(12) United States Patent
Easley et al.

(10) Patent No.: US 10,852,274 B2
(45) Date of Patent: Dec. 1, 2020

(54) DIFFERENTIAL CIRCUIT FOR BACKGROUND CORRECTION IN ELECTROCHEMICAL MEASUREMENTS

(71) Applicant: Auburn University, Auburn, AL (US)

(72) Inventors: Christopher J. Easley, Auburn, AL (US); Mark D. Holtan, Auburn, AL (US); Subramaniam Somasundaram, Auburn, AL (US)

(73) Assignee: Auburn University, Auburn, AL (US)

( * ) Notice: Subject to any disclaimer, the term of this patent is extended or adjusted under 35 U.S.C. 154(b) by 257 days.

(21) Appl. No.: 15/917,138

(22) Filed: Mar. 9, 2018

(65) Prior Publication Data

US 2018/0259483 A1  Sep. 13, 2018

Related U.S. Application Data

(60) Provisional application No. 62/469,333, filed on Mar. 9, 2017.

(51) Int. Cl.
  *G01N 27/48* (2006.01)
  *C12Q 1/6825* (2018.01)
  *G01N 27/327* (2006.01)

(52) U.S. Cl.
  CPC ........... *G01N 27/48* (2013.01); *C12Q 1/6825* (2013.01); *G01N 27/3276* (2013.01)

(58) Field of Classification Search
  CPC ... G01N 27/48; G01N 27/3276; C12Q 1/6825
  See application file for complete search history.

(56) References Cited

U.S. PATENT DOCUMENTS

| | | |
|---|---|---|
| 5,635,352 A | 6/1997 | Urdea et al. |
| 6,264,825 B1 | 7/2001 | Blackburn et al. |
| 6,350,580 B1 | 2/2002 | Sorge |
| 6,361,944 B1 | 3/2002 | Mirkin et al. |
| 6,506,564 B1 | 1/2003 | Mirkin et al. |
| 6,750,016 B2 | 6/2004 | Mirkin et al. |

(Continued)

FOREIGN PATENT DOCUMENTS

| | | |
|---|---|---|
| EP | 1198591 A1 | 4/2002 |
| EP | 1806414 A2 | 7/2007 |

(Continued)

OTHER PUBLICATIONS

P. Deman, et al. ("Continuous differential monitoring of the spent dialysate glucose level: clinical evaluation", Sensors and Actuators, B Chemical, 44(1-3): p. 304-308, Oct. (Year: 1997).*

(Continued)

*Primary Examiner* — J. Christopher Ball
(74) *Attorney, Agent, or Firm* — Shay Glenn LLP

(57) ABSTRACT

A method of target molecule detection includes simultaneously obtaining a first signal from a first working electrode and a second signal from a second working electrode, wherein the first signal is responsive to interaction of the first recognition element with the target molecule in a sample, and the second signal is indicative of background noise from the sample. The method further includes generating a modified signal that is proportional to an instantaneous difference between the first and second signals, wherein the modified signal indicates an amount of the target molecule present in the sample.

17 Claims, 10 Drawing Sheets

(56) References Cited

U.S. PATENT DOCUMENTS

| | | | |
|---|---|---|---|
| 6,767,702 | B2 | 7/2004 | Mirkin et al. |
| 6,773,884 | B2 | 8/2004 | Mirkin et al. |
| 6,984,491 | B2 | 1/2006 | Mirkin et al. |
| 7,005,265 | B1 | 2/2006 | Fan et al. |
| 7,169,556 | B2 | 1/2007 | Park et al. |
| 7,291,457 | B2 | 11/2007 | Miller et al. |
| 7,803,542 | B2 | 9/2010 | Xiao et al. |
| 7,807,352 | B2 | 10/2010 | Rabbani et al. |
| 8,003,374 | B2 | 8/2011 | Heeger et al. |
| 9,335,292 | B2 | 5/2016 | Hu et al. |
| 2001/0024788 | A1 | 9/2001 | Hashimoto |
| 2002/0006617 | A1 | 1/2002 | Fan et al. |
| 2002/0012943 | A1 | 1/2002 | Fowlkes et al. |
| 2002/0172953 | A1 | 11/2002 | Mirkin et al. |
| 2003/0022150 | A1 | 1/2003 | Sampson et al. |
| 2003/0077642 | A1 | 4/2003 | Fritsch et al. |
| 2003/0108922 | A1 | 6/2003 | Fritsch et al. |
| 2004/0106190 | A1* | 6/2004 | Yang ............... G01N 33/5438 435/287.2 |
| 2004/0191801 | A1 | 9/2004 | Heeger et al. |
| 2005/0096288 | A1 | 5/2005 | Guevara |
| 2005/0112605 | A1 | 5/2005 | Heeger et al. |
| 2005/0164286 | A1* | 7/2005 | O'uchi ................. C12M 1/34 435/6.11 |
| 2005/0202449 | A1 | 9/2005 | Getts et al. |
| 2006/0228703 | A1 | 10/2006 | Hartwich et al. |
| 2006/0234253 | A1 | 10/2006 | Hasui et al. |
| 2007/0084721 | A1 | 4/2007 | Hsung |
| 2007/0154909 | A1* | 7/2007 | Xiao ................ C12Q 1/6825 435/6.15 |
| 2007/0236224 | A1 | 10/2007 | Augustyniak |
| 2008/0076139 | A1 | 3/2008 | Singh |
| 2008/0302666 | A1 | 12/2008 | Benner et al. |
| 2009/0042735 | A1 | 2/2009 | Blair et al. |
| 2009/0305264 | A1 | 12/2009 | West et al. |
| 2010/0035248 | A1 | 2/2010 | Levicky et al. |
| 2010/0075319 | A1 | 3/2010 | Lohse |
| 2010/0248231 | A1 | 9/2010 | Wei et al. |
| 2010/0297654 | A1 | 11/2010 | Heyduk |
| 2011/0053788 | A1 | 3/2011 | Bamdad et al. |
| 2011/0143955 | A1 | 6/2011 | Weiner |
| 2012/0021426 | A1 | 1/2012 | Takoh et al. |
| 2012/0028242 | A1 | 2/2012 | Heyduk et al. |
| 2019/0382764 | A1 | 12/2019 | Easley et al. |

FOREIGN PATENT DOCUMENTS

| | | | |
|---|---|---|---|
| WO | WO01/040511 | A2 | 6/2001 |
| WO | WO01/051665 | A2 | 7/2001 |
| WO | WO01/073123 | A2 | 10/2001 |
| WO | WO02/018643 | A2 | 3/2002 |
| WO | WO02/046472 | A2 | 6/2002 |
| WO | WO03/035829 | A2 | 5/2003 |
| WO | 2004/023128 | | 3/2004 |
| WO | WO2008/001376 | A2 | 1/2008 |
| WO | WO2011/017382 | A2 | 2/2011 |
| WO | WO2011/050069 | A1 | 4/2011 |
| WO | WO2011/161420 | A2 | 12/2011 |

OTHER PUBLICATIONS

Arroyo-Curras et al.; Real-time measurement of small molecules directly in awake, ambulatory animals; Proceedings of the National Academy of Sciences; 114(4); pp. 645-650; Jan. 24, 2017.

Bonham et al.; Detection of IP-10 protein marker in undiluted blood serum via an electrochemical e-dna scaffold sensor; Analyst; 138(19); pp. 5580-5583; 9 pages (Author Manuscript); Oct. 7, 2013.

Campos et al.; Amperometric detection of lactose using ?-galactosidase immobilized in layer films; ACS Applied Materials and Interfaces; 6(14); pp. 11657-11664; 8 pages (Author Manuscript); Jul. 11, 2014.

Carrillo et al.; The multiple sequence augment problem in biology; SIAM Journal on Applied Mathematics; 48(5); pp. 1073-1082; Oct. 1988.

Cash et al.; An electrochemical sensor for the detection of protein-small molecule interactions directly in serum and other complex matrices; Journal of the American Chemical Society; 131(20); pp. 6955-6957; May 4, 2009.

Dirks et al.; A partition function algorithm for nucleic secondary structure including pseudoknots; Journal of Computational Chemisrty; 24(10); pp. 1664-1677; Oct. 2003.

Dirks et al.; An algorithm for computing nucleic acid base-pairing proabilities including pseudoknots; Journal of Computational Chemisrty; 25(10); pp. 1295-1304; Jul. 30, 2004.

Dirks at al; Paradigms for computational nucleic acid design; Nucleic Acid Research; 32(4); pp. 1392-1403; Feb. 27, 2004.

Dryden et al.; Dstat: A versatile, open-source potentiostat for electroanalysis and integration; PLOS One; DOI: 10.1371/journal.pone.0140349; 17 pages; Oct. 28, 2015.

Fan et al.; Electrochemical interrogation of conformational changes as a reagentless method for the sequence-specific detection of dna; Proceedings of the National Academy of Sciences; 100(16); pp. 9134-9137; Aug. 5, 2003.

Ferapontova et al.; An ma aptamer-based electrochemical biosensor for detection of theophylline in serum; Journal of the American Chemical Society; 130(13); pp. 4256-4258; Apr. 2, 2008.

Ferguson et al.; Real-time, aptamer-based tracking of circulating therapeutic agents in living animals; Science Translational Medicine: 5(213); pp. 213ra165, 11 pages; Nov. 27, 2013.

Hu et al.; A reusable electrochemical proximity assay for highly selective, real-time protein quantitation in biological matrices; Journal of the American Chemical Society; 136(23); pp. 8487-8474; May 30, 2014.

Idili et al.; Folding-upon-binding and signal-on electrochemical dna sensor with high affinity and specificity; Analytical Chemistry; 86(18); pp. 9013-9019; Jul. 3, 2014.

Jeyarajah et al.; Lipoprotein particle analysis by nuclaer magnetic resoance spectroscopy; Clinics in Laboratory Medicine; 26(4); pp. 847-870; Dec. 2006.

Kaess et al.; The lipoprotein sub-fraction profile hertability and indentification of quantitative trait loci; Journal of Lipid Research; 49(4); pp. 715-723; Apr. 2008.

Kang et al.; Comparing the properties of electrochemical-based dna sensors employing different redox tags, Analytical Chemistry; 81(21); pp. 9109-9113; 12 pages (Author Manuscript); Oct. 7, 2009.

Kick et al.; EGNAS: an exhaustive dna sequence design algorithm; BMC Bioinformatics; 13(1); pp. 138; 17 pages; http://www.biomedcentral.com/1471-2105/13/138; Dec. 2012.

Labib et al.; Electrochemical methods for the analysis of clinically relevant biomolecules; Chemical Reviews; 116(16); pp. 9001-9090; Jul. 18, 2016.

Li et al.; Target-responsive structural switching for nucleic acid-based sensors, Accounts of Chemical Research; 43(5); pp. 631-641; Mar. 11, 2010.

Liu et al.; Aptamer-based electrochemical biosensors for interferon gamma detection; Analytical Chemistry; 82(19); pp. 8131-8136; Sep. 3, 2010.

Mage; Closed-loop control of circulating drug levels in live animals; Nature Biomedical Engineering; 1(5); DOI:10.1038/s415551-017-0070, 10 pages; May 2017.

Mahshid et al.; A highly selective electrochemical dan-based sensor that employs steric hindrance effects to detect proteins directly in whole blood; Journal of the American Chemical Society: 137(50); pp. 15596-15599; Sep. 24, 2015.

Mahshid et al.; Biomolecular steric hindrance effects are enhanced on nanostructured microelectrodes; Analytical Chemistry; 89(18); pp. 9751-9757; Sep. 5, 2017.

Mahshid et al.; Electrochemical dna-based immunoassay that employs steric hindrance to detect small molecules directly in whole blood; AACS Sensors; 2(6); pp. 718-723; May 25, 2017.

Needleman et al.; A general method applicable to the search for similarities in the amino scid sequence of two proteins; Journal of Molecular Biology; 48(3); pp. 443-453; Mar. 1970.

Sacks et al.; Clinical review 163: cardiovascular endocrinology: low-density lipoprotein size and cardiovascular disease: a reap-

(56) References Cited

OTHER PUBLICATIONS praisal; The Journal of Clinicai Endocrinology and Metabolism; 88(10); pp. 4525-4532; Oct. 2003.
Schoukroun-Barnes et al.; Reagentless, structure-switching, electrochemical aptamer-based sensors; Annual Review of Analtyical Chemistry; 9(1); pp. 163-181; 23 pages (Author Manuscript) Jun. 2016.
Silva etal.; Gold electrode modified by self-assembled monolayers of thiolis to determine dna sequences hybridization; Journal of Chemical Sciences; 122(6); pp. 911917; Nov. 2010.
Somasundaram et al.; Understanding signal and background in a thermally resolved, single-branched dna assay using sqaure wave voltammetry; Analytical Chemistry; 90(50); pp. 3584-3591; 18 pages (Author Manuscript); Jan. 31, 2018.
Turner; Biosensors: sense and sensibility; Chemical Society Reviews; 42(8): pp. 3184-3196; (year of pub. sufficiently earlier than effective US filing date and any foreign priority date) 2013.
White et al.; Exploiting binding changes in probe flexibility for the optimization of electrochemical biosensors; Analytical Chemistry; 82(1); pp. 73-76; 10 pages (Author Manuscript); Dec. 10, 2009.
Wolfe et al.; Constrained multistate sequence design for nucleic acid reaction pathway engineering; Journal of American Chemical Society; 139(8); pp, 3134-3144; Feb. 13, 2017.
Wolfe et al.; Sequence design for a test tube of interacting nucleic acid strands; ACS Synthetic Biology; 4(10); pp. 1086-1100; Oct. 20, 2014.
Xiao et al.; A reagentless signal-on architecture for electronic, aptamer-based sensors via target-induced strand displacement; Journal of the American Chemical Society; 127(51); pp. 17990-17991; (Author Manuscript); Dec. 28, 2005.
Zadeh et al.; Nucleic acid sequence design via efficient ensemble defect optimization; Journal of Computational Chemistry; 32(3); pp. 439-452; Feb. 2011.
Zadeh et al.; NUPACK: analysis and design of nucleic acid systems; Journal of computattional Chemistry; 32(1); pp. 170-173; Jan. 15, 2011.
Zhou et al.; Steric hindrance assay for secreted factors in stem cell culture; ACS Sensors; 2(4); pp. 495-500; Apr. 17, 2017.
Zymek et al.; The role of platelet-derived growth factor signal in healing mycardial infarcts; Journal of the American college of Cardiology; 48(11); pp. 2315-2323; Dec. 5, 2006.
Inapuri et al.: U.S. Appl. No. 16/629,223 entitled "Aptamers for measuring lipoprotein levels," filed Jan. 7, 2020.
Sigma-Aldrich; Self-assembled monolayers: advantages of pure alkanethiots; 4 pages retrieved from the internet (https://www.sigmaaldrich.com/technical-documents/articles/material-matters/self-assembled-monolayers.html) on Dec. 10, 2019.
International Search Report/Written Opinion prepared for PCT/US2018/021773, dated Jun. 14, 2018.
Deng et al.; Sensitive bifunctional aptamer-based electrochemical biosensor for small molecules and protein; Analytical Chemistry; 81(24); pp. 9972-9978; Nov. 19, 2009.

Du et al.; Multifunctional label-free electrochemical biosensor based on an integrated aptamer; Analytical Chemistry; 80(13); pp. 5110-5117; Jun. 4, 2008.
Fan et al.; A Competitor-switched electrochemical sensor for detection of dna: Chin. J. Chem.; 28; pp. 1978-1982; (year of pub. sufficiently earlier than effective US filing date and any foreign priority date) 2010.
Huang et al.; Random wlak on a leash: a simple single-molecule diffusion model for surface-tethered redox molecules with flexible linkers; Journal of the American Chemical Society; 135(34); pp. 12808-12817; Aug. 20, 2013.
Li et al.; A simple assay to amplify the electrochemical signal by the aptamer based biosensor modified with CdS hollow nanospheres; Biosensors and Bioelectronics; 26(8); pp. 3531-3535; Apr. 15, 2011.
Lin et al.; Label-free aptamer-based electrochemical impedance biosensor for 17? estradiol; Analyst; 137(4); pp. 819-822; Feb. 2012.
Lu et al.; Aptamer-based electrochemical sensors that are not based on the target binding-induced conformational change of aptamers; Analyst; 133(9); pp. 1256-1260; Sep. 2008.
Lubin et al.; Effects of probe length, probe geometry, and redox-tag placement on the performance of the electtrochemical e-dna sensor; Analytical Chemistry; 81(6); pp. 2150-2158; Feb. 12, 2009.
Suna et al.; 1H NMR metabolomics of plasma lipoprotein subclasses; elucidation of metabolic clustering by self-organizing maps; NMR in Biomedicine; 20(7); pp. 658-672; Nov. 2007.
Tong et al.; Simply amplified electrochemical aptasensor of ochratoxin a based on exonuclease-catalyzed target; Biosensors and Bioelectronics; 29(1); pp. 97-101; Nov. 15, 2011.
Wang et al.; A sensitive ligase-based atp electrochemical assay using molecular beacon-like dna; Biosensor and Bioelectronics; 25(9); pp. 2101-2106; May 2010.
Wu et al.; Reusable electrochemical sensing platform for highly sensitive detection of small molecules based on structure-switching signal aptamers; Analytical Chemistry; 79(7); pp. 2933-2939; Apr. 2007.
Xiao et al.; Preparation of electrode-immobilized, redox-modified oligonucleotides for electrochemical dna and aptamer-based sensing; Nature Protocols; 2(11); pp. 2875-2880; Nov. 2007.
Yeung et al.; Electrochemical real-time polymerase chain reaction; Journal of the American Chemical Society; 128(41); pp. 13374-13375; Oct. 18, 2006.
Zhang et al.; Electrochemical aptasensor based on proximity-dependent surface hybridization assay for protein detection; Electroanalysis; An International Journal Devoted to Fundamental and Practical Aspects of Electroanalysis; 21(11), pp. 1327-1333, Jun. 2009.
Zhang et al.; Electrochemical aptasensor based on proximity-dependent surface hybridization assay for single-step, reusable, sensitive protein detection; Journal of the American Chemical Society; 129(50); pp. 15448-15449; Published on line Nov. 22, 2007.
Zhao et al.; A label-free electrochemilumescent sensor for atp detection based on atp-dependent ligation; Talanta; 154; pp. 492-497; Jul. 2016.

* cited by examiner

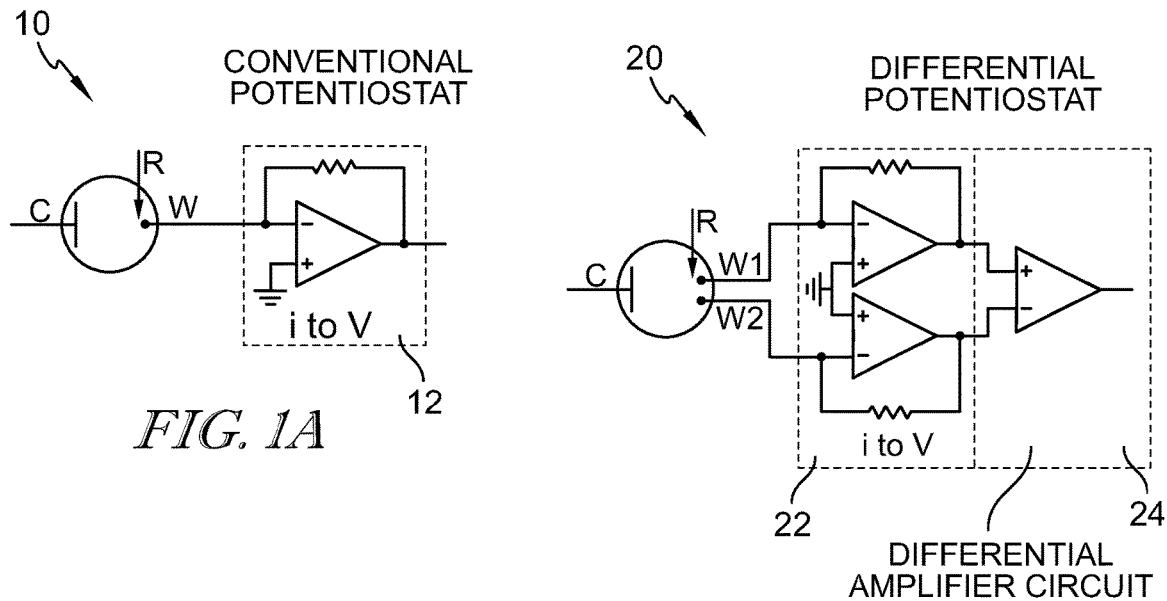
FIG. 1A
FIG. 1B
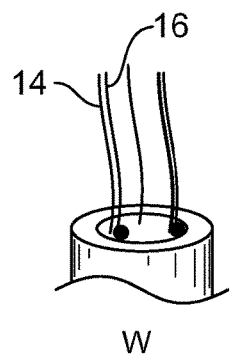
FIG. 1C
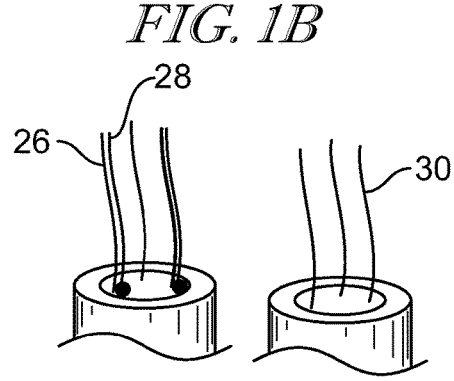
FIG. 1D
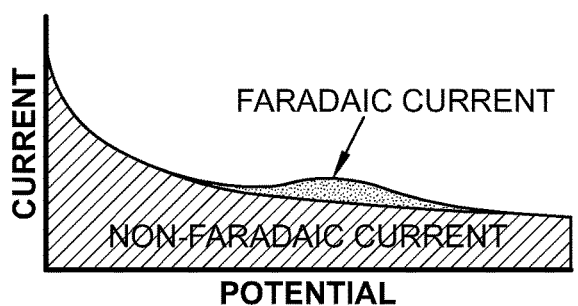
FIG. 1E
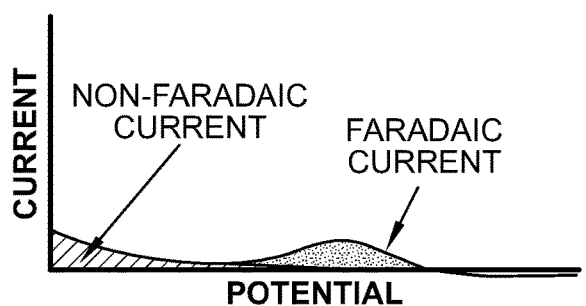
FIG. 1F

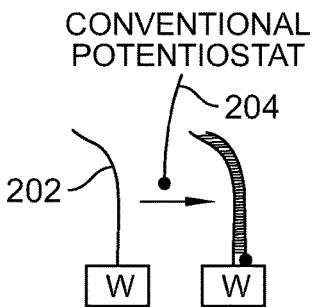
FIG. 2A
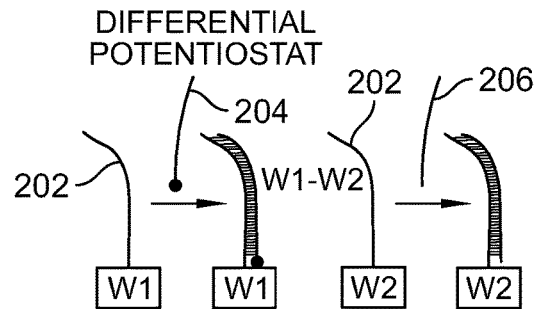
FIG. 2B
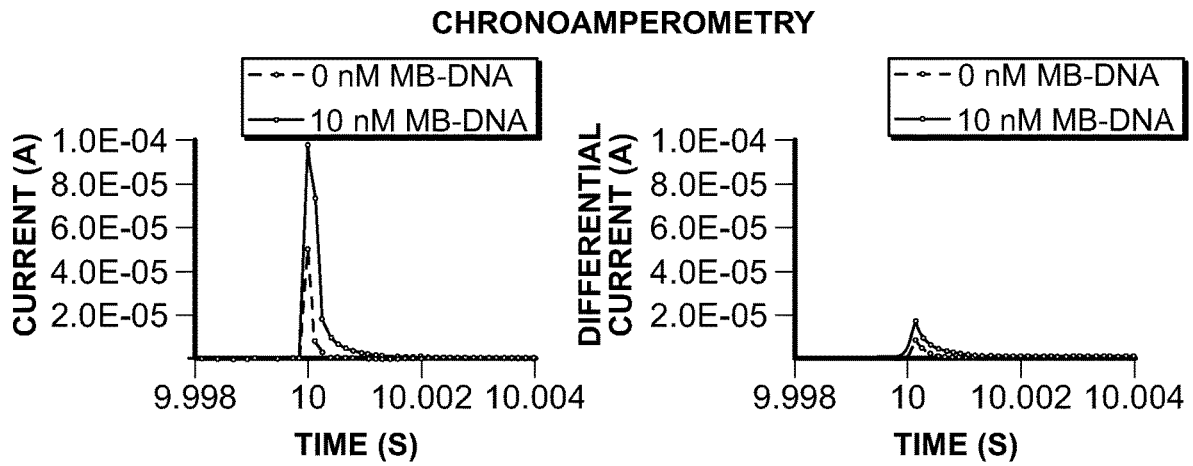
FIG. 2C
FIG. 2D
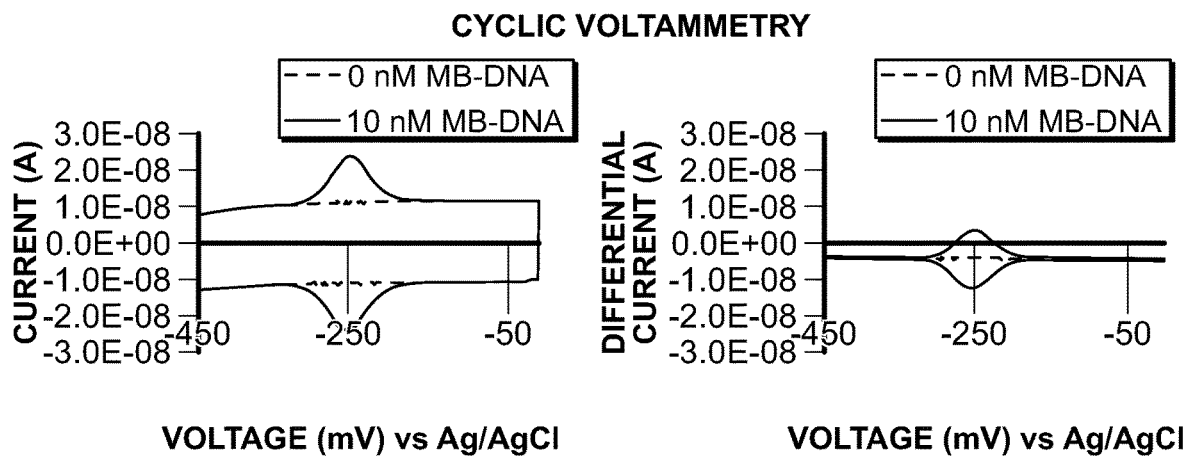
FIG. 2E
FIG. 2F

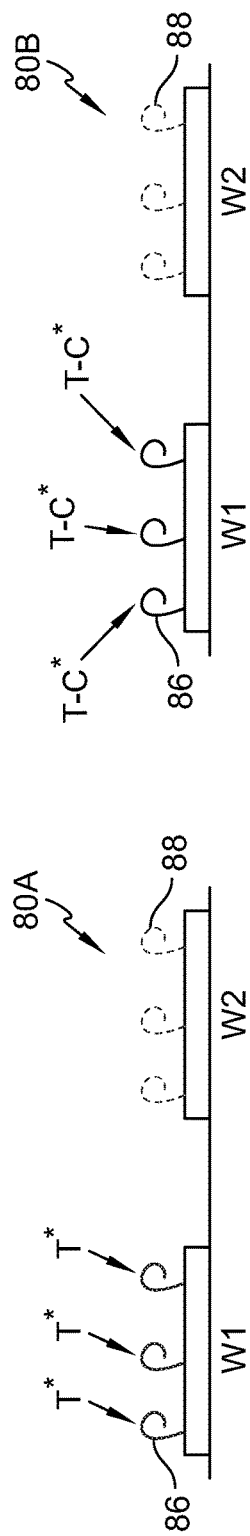
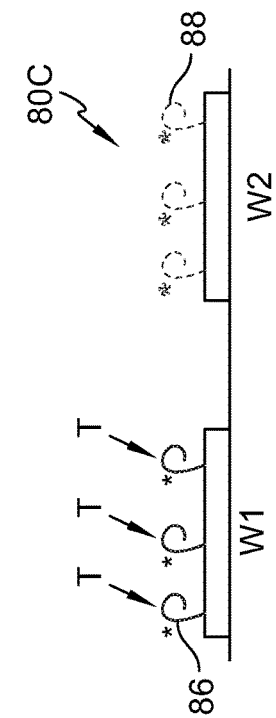
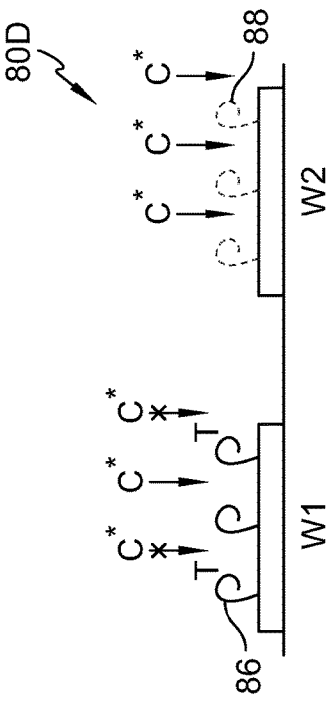
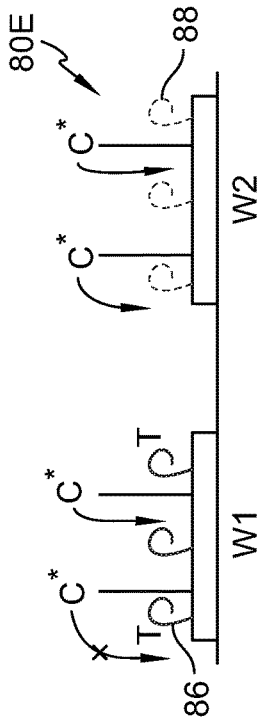

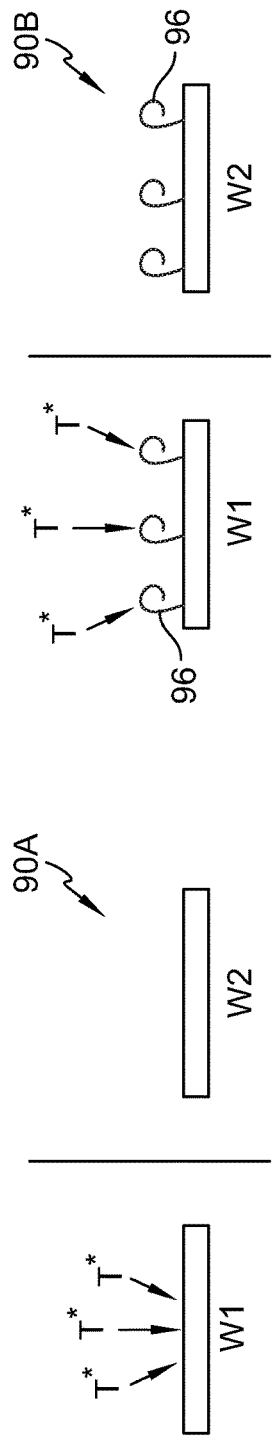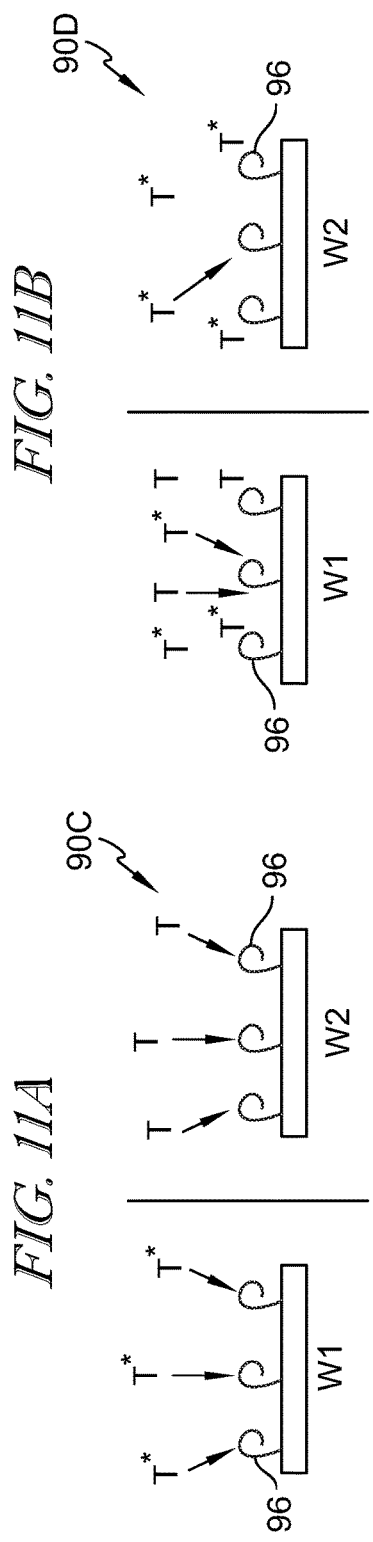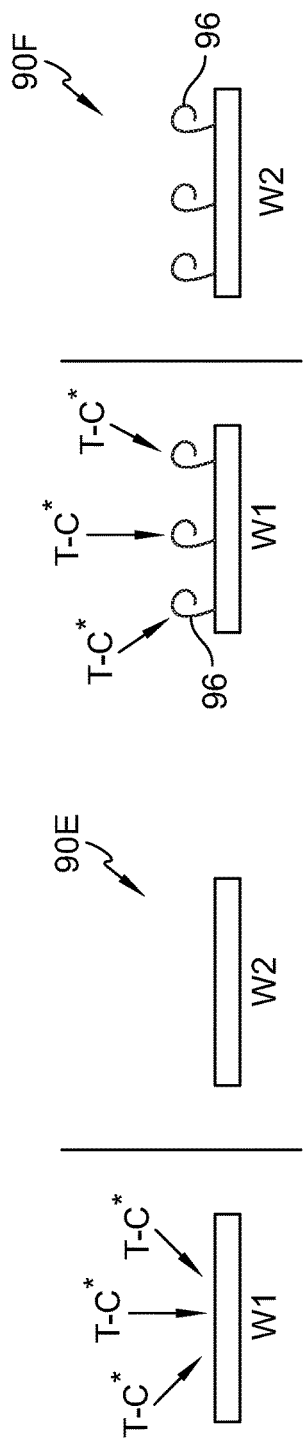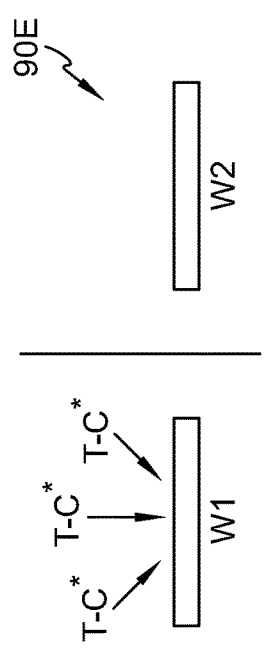

DIFFERENTIAL CIRCUIT FOR BACKGROUND CORRECTION IN ELECTROCHEMICAL MEASUREMENTS

CROSS-REFERENCE TO RELATED APPLICATION

This application claims priority under 35 U.S.C. § 119(e) to U.S. Provisional Application No. 62/469,333 filed Mar. 9, 2017, which is expressly incorporated by reference herein.

GOVERNMENT RIGHTS

This invention was made with government support under grant number CBET-1403495 awarded by the National Science Foundation. The government has certain rights in the invention.

TECHNICAL FIELD

The present disclosure relates generally to systems and methods for electrochemical detection of a target molecule.

BACKGROUND

A potentiostat is an electronic device used for electroanalytical experiments. A conventional potentiostat is typically a three electrode system (in particular, a working electrode, a reference electrode, and a counter electrode) that controls the voltage difference between the working electrode and the reference electrode. The potentiostat outputs voltammetric data, which typically includes both faradaic and non-faradaic currents. Faradaic current is a concentration-dependent signal indicative of information about a target molecule, whereas non-faradaic current indicates background (e.g., capacitive current and/or white noise). In order to obtain a true concentration-dependent signal, data collected using a conventional potentiostat is processed post-experiment rather than during the experiment to obtain a corrected faradaic current. As such, the conventional potentiostat may impose upper limits on sensitivity settings when non-Faradaic currents are high.

SUMMARY

According to one aspect of the disclosure, an apparatus for target molecule detection includes a sample cell configured to receive a sample, a reference electrode in communication with the sample cell, a counter electrode in communication with the sample cell, a first working electrode, a second working electrode, and a differential amplifier circuit. The first working electrode is in communication with the sample cell and is coated with a first recognition element that is to interact with a target molecule in the sample. The first working electrode is configured to measure a first signal responsive to interaction of the first recognition element with the target molecule. The second working electrode is in communication with the sample cell is not coated with the first recognition element. The second working electrode is configured to measure a second signal indicative of background noise from the sample. The differential amplifier circuit is configured to generate a modified signal that is proportional to a difference between the first and second signals. The modified signal indicates an amount of the target molecule present in the sample.

In some embodiments, the first and second working electrodes are prepared using the same technique(s) other than the coating or non-coating with the first recognition element.

In some embodiments, the first recognition element that is labeled with an electrochemically active component. The second working electrode is coated with a second recognition element that is to interact with the target molecule and is unlabeled with an electrochemically active component.

In some embodiments, the target molecule is electrochemically active or is labeled with an electrochemically active component.

In some embodiments, the background noise includes at least one of capacitive current, electrical noise, environmental noise, chemical interferences, biological interferences, and temperature effects.

In some embodiments, the modified signal is proportional to an instantaneous difference between the first and second signals.

In some embodiments, the apparatus further includes a first current-to-voltage converter circuit and a second current-to-voltage converter circuit. The first current-to-voltage converter circuit is coupled to the first working electrode and is configured to convert the first signal to a first voltage signal, wherein the first signal is current measured at the first working electrode. The second current-to-voltage converter circuit is coupled to the second working electrode and is configured to convert the second signal to a second voltage signal, wherein the second signal is current measured at the second working electrode. In such embodiments, the modified signal generated by the differential amplifier circuit is proportional to a voltage difference between the first and second voltage signals.

According to another aspect, an apparatus for target molecule detection includes a first sample cell configured to receive a target molecule in a medium, a second sample cell configured to receive the medium, a reference electrode in communication with the first and second sample cells, a counter electrode in communication with the first and second sample cells, a first working electrode, a second working electrode, and a differential amplifier circuit. The first working electrode is in communication with the first sample cell and is configured to measure a first signal responsive to interaction of the first recognition element with the target molecule. The second working electrode is in communication with the second sample cell and is configured to measure a second signal indicative of background noise from the medium. The differential amplifier circuit is configured to generate a modified signal that is proportional to a difference between the first and second signals. The modified signal indicates an amount of the target molecule present in the first sample cell.

In some embodiments, the first and second working electrodes are prepared using the same technique(s).

In some embodiments, the target molecule is labeled with an electrochemically active component.

In some embodiments, the second sample cell is configured to receive a target molecule in the medium. In such embodiments, the first working electrode is coated with a first recognition element that is labeled with an electrochemically active component and interacts with the target molecule; and the second working electrode is coated with a second recognition element that is unlabeled with an electrochemically active component and interacts with the target molecule In some embodiments, the second working electrode is coated with a second recognition element that is to interact with the medium to determine background noise.

In some embodiments, the second signal indicates background noise from the medium. The background noise includes at least one of capacitive current, electrical noise, environmental noise, chemical interferences, biological interferences, and temperature effects.

In some embodiments, the modified signal is proportional to an instantaneous difference between the first and second signals.

In some embodiments, the first sample cell further includes a recognition element which is an electrochemically active molecule. The second sample cell does not include the recognition element.

In some embodiments, the apparatus further includes a first current-to-voltage converter circuit and a second current-to-voltage converter circuit. The first current-to-voltage converter circuit is coupled to the first working electrode and is configured to convert the first signal to a first voltage signal, wherein the first signal is current measured at the first working electrode. The second current-to-voltage converter circuit is coupled to the second working electrode and is configured to convert the second signal to a second voltage signal, wherein the second signal is current measured at the second working electrode. In such embodiments, the modified signal generated by the differential amplifier circuit is proportional to a voltage difference between the first and second voltage signals.

According to another aspect, a method of target molecule detection includes simultaneously obtaining a first signal from a first working electrode and a second signal from a second working electrode, wherein the first signal is responsive to interaction of the first recognition element with the target molecule in a sample, and the second signal is indicative of background noise from the sample, and generating a modified signal that is proportional to an instantaneous difference between the first and second signals, wherein the modified signal indicates an amount of the target molecule present in the sample.

In some embodiments, the method further includes converting the first signal to a first voltage signal, the first signal being current measured at the first working electrode, and converting the second signal to a second voltage signal, the second signal being current measured at the second working electrode. In such embodiments, the modified signal is proportional to an instantaneous voltage difference between the first and second voltage signals.

In some embodiments, the first and second working electrodes are both in communication with a sample cell receiving the sample. The first working electrode is coated with a recognition element that is to interact with a target molecule present in the sample, wherein the target molecule is labeled with an electrochemically active component. The second working electrode is not coated with a recognition element or is coated with a similar element that does not interact with the target molecule.

In some embodiments, the first and second working electrodes are both in communication with a sample cell receiving the sample. The first working electrode is coated with a first recognition element that is labeled with an electrochemically active component and interacts with the target molecule. The second working electrode is coated with a second recognition element that is unlabeled with an electrochemically active component and interacts with the target molecule.

In some embodiments, the first working electrode is in communication with a first sample cell receiving a target molecule in a medium, wherein the target molecule is labeled with an electrochemically active component. The second working electrode is in communication with a second sample cell receiving the medium but not the target molecule.

In some embodiments, the first working electrode is in communication with a first sample cell receiving a target molecule in a medium, wherein the first working electrode is coated with a first recognition element that is labeled with an electrochemically active component and interacts with the target molecule. The second working electrode is in communication with a second sample cell receiving the target molecule in the medium, wherein the second working electrode is coated with a second recognition element that is to interact with the target molecule and is unlabeled with an electrochemically active component.

BRIEF DESCRIPTION OF THE DRAWINGS

The detailed description particularly refers to the following figures, in which:

FIGS. 1A-1F illustrate comparisons between a conventional potentiostat and a differential potentiostat;

FIGS. 2A-2F illustrate chronoamperometry and cyclic voltammetry measurements for surface confined nucleic acid based bioassays conducted using the conventional potentiostat of FIG. 1A and the differential potentiostat of FIG. 1B;

FIGS. 10A-10E are diagrammatic representations illustrating exemplary embodiments of working electrodes that may be used with the system of FIG. 8; and FIGS. 11A-11J are diagrammatic representations illustrating exemplary embodiments of working electrodes that may be used with the system of FIG. 9.

DETAILED DESCRIPTION OF THE DRAWINGS

Figure 3A:
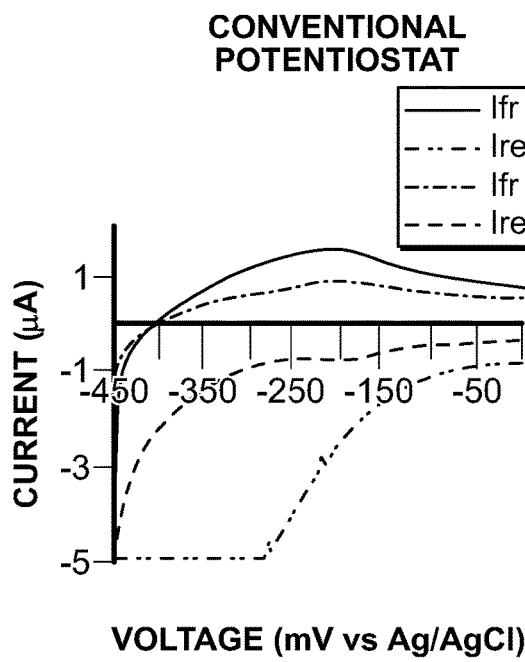
FIGS. 3A-3D illustrate square-wave voltammetry measurements obtained with the conventional potentiostat and the differential potentiostat in accordance with FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Referring now to FIGS. 1A-1F, comparisons between a conventional potentiostat 10 and a differential potentiostat 20 is shown. (Each of FIGS. 1A, 1C, and 1E relate to the conventional potentiostat 10, while each of FIGS. 1B, 1D, and 1F relate to the differential potentiostat 20.) A potentiostat is an electronic device electrochemical analysis (e.g., for voltammetry, amperometry, and other related techniques) that controls the voltage difference between a working electrode and a reference electrode. The data typically includes of both faradaic and non-faradaic currents. Faradaic current is a concentration-dependent signal indicative of information about a target molecule, whereas non-faradaic current indicates background (e.g., capacitive current and/or white noise).

FIGS. 1A and 1B illustrate schematic circuit diagrams of the conventional potentiostat 10 and the differential potentiostat 20. As shown in FIG. 1A, the conventional potentiostat 10 typically includes a reference electrode R, a counter electrode C, and a working electrode W connected to a current-to-voltage converter circuit 12. The working electrode W is in communication with a sample cell that is configured to receive a sample with a target molecule and is configured to generate a signal indicative of a current at the working electrode W. For example, as diagrammatically shown in FIG. 1C, the working electrode W may be coated with an unlabeled recognition element 14 to measure the sample signal from a labeled target molecule 16.

Accounting for background noise with the conventional potentiostat 10 is difficult. Commonly, users of the conventional potentiostat 10 must repeat each experiment without the target molecule in the sample cell, using the same working electrode W, in order to measure a background signal. However, this background signal may not accurately represent the background noise in the sample cell with the target molecule due to changing conditions between experiments. In such embodiments, the data collected using conventional potentiostat 10 is subsequently modified by software to subtract non-faradaic current from the faradaic current to obtain a corrected, concentration-dependent signal. Because the baseline correction must be performed after the multiple experiments, rather than during a single experiment, the conventional potentiostat 10 imposes upper limits on sensitivity settings when non-Faradaic currents are high.

In contrast, as shown in FIG. 1B, the differential potentiostat 20 includes a reference electrode R, a counter electrode C, two working electrodes W1, W2, two current-to-voltage converter circuits 22 (each of which is connected to a respective working electrode), and a differential amplifier circuit 24. Each working electrode W1, W2 is in communication with a sample cell that is configured to receive a sample and is configured to generate a signal indicative of a current at the corresponding working electrode. Specifically, the first working electrode W1 is configured to measure a first signal responsive to a target molecule in the sample, whereas the second working electrode W2 is configured to measure a second signal indicative of background (e.g., capacitive current) for background correction. To do so, the first and second working electrodes W1, W2 are prepared using the same technique, except that only the first working electrode W1 is coated with a recognition element. Alternatively, the first and second working electrodes W1, W2 are prepared using the same technique, except that each working electrode W1, W2 is coated with a different recognition element. For example, as diagrammatically shown in FIG. 1D, the first working electrode W1 may be coated with an unlabeled recognition element 26 and the second working electrode W2 may be coated with a similar or equivalent an unlabeled recognition element 30. In the illustrative embodiment, the recognition element 26 is configured to interact with the target molecule 28, while the recognition element 30 is configured to interact with the sample medium to represent the background. The target molecule 28 is labeled and is electrochemically active. It should be appreciated that the labeled target molecule 28 is only added to interact with the recognition element 26 on the first working electrode W1, and the target molecule interaction will influence a signal that represents the target molecule and any background effects. The recognition element 30 on the second working electrode W2 interacts only with the sample medium, which will influence a signal that represents only the background effects. The first and second signals are fed into the differential amplifier circuit 24, which is configured to generate a modified signal that is proportional to a difference between the first and second signals and indicates of an amount of the target molecule present in the sample. In other words, the differential potentiostat 20 is configured to amplify only a target-dependent component of the first signal generated at the first working electrode W1 without background noise.

As shown in FIGS. 1E and 1F, the voltammetric data obtained using the conventional potentiostat 10 and the differential potentiostat 20 include both faradaic and non-faradaic background currents. As discussed above, the differential potentiostat circuit 20 is configured to simultaneously collect both signal and baseline electrode measurements with a pair of working electrodes W1, W2 and perform an on-board analog subtraction. To do so, as shown in FIG. 1B, the analog signal and baseline electrode measurements are converted into voltages using the respective current-to-voltage converters 22, which are fed into the differential amplifier circuit 24 to output a corrected signal. As a result, the non-faradaic background current obtained using the differential potentiostat 20 is significantly reduced or eliminated (FIG. 1F) as compared to the non-faradaic background current obtained using the conventional potentiostat 10 (FIG. 1E). This allows on-chip amplification of the important signal components and prevents amplification of the non-faradaic current and white noise. Consequently, wider detection ranges, higher sensitivities, and larger electrodes can be used with the differential potentiostat 20 as compared to a conventional potentiostat 10.

It should be appreciated that, in some embodiments, the differential potentiostat 20 may be modified to detect multiple target molecules. In such embodiments, the differential potentiostat 20 may include more than one pair of working electrodes W1, W2, where each working electrode is connected to a respective current-to-voltage converter circuit 22, and a reference electrode R, a counter electrode C, and a differential circuit. In some embodiments, a different differential circuit may be provided for each pair of working electrodes W1, W2.

Referring now to FIGS. 2A-2F, chronoamperometry and cyclic voltammetry measurements for surface confined nucleic acid based bioassays obtained using the conventional potentiostat 10 and the differential potentiostat 20 are shown. (Each of FIGS. 2A, 2C, and 2E relate to the conventional potentiostat 10, while each of FIGS. 2B, 2D, and 2F relate to the differential potentiostat 20.) Chronoamperometry and cyclic voltammetry are two widely used electrochemical quantification methods that undergo continuous measurement to obtain information about target molecules. However, the sensitivity of these electrochemical quantification methods is challenged by non-faradaic or capacitance current. More complicated electrochemical quantification methods, such as pulse voltammetry technique, have been developed to perform non-continuous measurements in effort to reduce the capacitance current. Even though pulse voltammetry is more sensitive than chronoamperometry and cyclic voltammetry, the calculation of electrochemical signaling units from the signal output is not direct due to the entanglement of multiple mathematical assumptions. As discussed further below, the differential potentiostat 20 may be used to overcome such challenges in chronoamperometry and cyclic voltammetry to suppress non-faradaic current without disturbing faradaic current.

Additionally, the differential potentiostat 20 may be used with surface confined nucleic acid based bioassays to overcome the similar problem. Surface confined nucleic acid based bioassays may be used for quantitative electrochemical detection of DNA hybridization, aptamer-target binding, or antibody-target binding. However, the resulting data also include a background signal which fundamentally degrades the limit of detection. Having at least two working electrodes to simultaneously collect signal and background allows hardware subtraction of the analog signals while collecting the measurement to eliminate both non-faradaic and baseline artifacts and reduce noise.

In the illustrative embodiment, the conventional potentiostat 10 is configured to detect interactions between a recognition element 202 that is immobilized on a working electrode W and a labeled target molecule 204, which is electrochemically active and is added to a sample medium. In one embodiment, a 2 mm diameter gold working electrode W was prepared from gold sputtered microscopic slides through photolithography and was immobilized with 40 nucleotide DNA by self-assembled monolayer through thiol-gold chemistry. In that embodiment, the chronoamperometry and cyclic voltammetry measurements were collected for a predefined period of time which represent a capacitance current or baseline shown as 0 nM MB-DNA plots in FIGS. 2C and 2E.

In another embodiment, using the differential potentiostat 20, two 2 mm diameter gold working electrodes W1, W2 were both prepared from gold sputtered microscopic slides through photolithography and were immobilized with 40 nucleotide DNA by self-assembled monolayer through thiol-gold chemistry. As shown in FIG. 2B, a labeled target molecule 204 was exposed to the first working electrode W1, while an unlabeled target molecule 206 was exposed to the second working electrode W2. It should be appreciated that the chronoamperometry and cyclic voltammetry measurements will only be affected by a target interaction with the target molecule that is electrochemically active or is labeled with an electrochemically active component. As shown in FIGS. 2D and 2F, the chronoamperometry and cyclic voltammetry measurements were collected without any target molecules which represent a capacitance current or baseline shown as 0 nM MB-DNA plots. As can be seen in 0 nM MB-DNA plots in FIGS. 2C-2F, the capacitance current obtained using the differential potentiostat 20 was significally lowered as compared to the capacitance current obtained using the conventional potentiostat 10 for both voltammetry techniques.

Subsequently, for conventional potentiostat 10, 10 nM concentration of the labeled target molecule 204 (e.g., methylene blue conjugated DNA (MB-DNA)), which is complementary to the recognition element 202 (e.g., surface immobilized thiolated-DNA), was introduced to the sample medium that contained the working electrode W. The chronoamperometry and cyclic voltammetry measurements were again collected for a predefined period of time, which is shown as 10 nM MB-DNA plots in FIGS. 2C and 2E. For the differential potentiostat 20, 10 nM concentration of the labeled target molecule 204 (e.g., MB-DNA) was introduced to the first working electrode W1. Simultaneously, to counteract the shift in the capacitance current by MB-DNA addition to the first working electrode W1, 10 nM concentration of an unlabeled target molecule 206 (e.g., DNA of the same sequence excluding methylene blue), which is complementary to the recognition element 202 (e.g., surface immobilized thiolated-DNA), was introduced to the second working electrode W2. This ensures that no target-dependent faradaic current is generated at the second working electrode W2, yet similar or equivalent non-faradaic current is generated at second working electrode W2. The chronoamperometry and cyclic voltammetry measurements were again collected for a predefined period of time, which is shown as 10 nM MB-DNA plots in FIGS. 2D and 2F.

As discussed above, the voltammetry measurements using the differential potentiostat 20 represents a difference between the current measurements at the first working electrode W1 and the second working electrode W2. As shown in 10 nM MB-DNA plots in FIGS. 2C-2F, the differential potentiostat 20 generates the faradaic current with minimized background (e.g., capacitance, noise, etc.) as compared to the conventional potentiostat 10. It should be noted that the faradaic current generated using the differential potentiostat 20 is lower at least partially because the capacitance current is eliminated prior to amplification, which prevents amplification of the non-faradaic current and white noise. As such, the differential potentiostat configuration with two working electrodes W1, W2 and the differential amplifier circuit 24 significantly improves signal-to-noise ratio and sensitivity over the conventional potentiostat 10. Various electrochemical analysis methods, e.g. Fourier analysis of chronoamperometry data or AC voltammetry, should also benefit from the present invention.

Referring now to FIGS. 3A-3D, a comparison of square wave voltammetry measurements using the conventional potentiostat 10 and the differential potentiostat 20 is shown. (Both of FIGS. 3A and 3C relate to the conventional potentiostat 10, while both of FIGS. 3B and 3D relate to the differential potentiostat 20.) A variety of high performance assay formats exploit quantitative electrochemical detection of DNA hybridization or aptamer-target binding using square wave voltammetry. Square-wave voltammetry is one of the pulse voltammetry techniques, where the potential is swept across a range with a square-wave pattern, and current measurements are done at the end of each square-wave before the next pulse, giving both a forward and reverse current ($I_{fr}$ and $I_{re}$). Square-wave voltammetry reduces capacitance current background in the final readout by waiting until the capacitance current decays significantly; however, a loss of Faradaic current also occurs simultaneously, particularly in surface-confined measurements. Additional reductions in background in square-wave voltammetry are accomplished through a software-based subtraction after all the data is collected. Because the baseline correction is performed post-experiment rather than during the experiment, the conventional potentiostat 10 may impose upper limits on sensitivity settings when non-Faradaic currents are high.

In one embodiment, the same working electrodes and identical samples were tested at different sensitivity settings using the conventional potentiostat 10 and the differential potentiostat 20. It should be appreciated that, as used in the present disclosure, the phrase "same working electrodes" refers to multiple working electrodes that have been prepared from the same material(s) using the same technique(s). However, the "same working electrodes" may be subsequently coated with different recognition elements (or a lack thereof) in order to differently interact with the target molecules. In other words, the phrase "same working electrodes" does not indicate that those working electrodes are coated with the same recognition element and the same electrochemically active component.

Figure 3B:
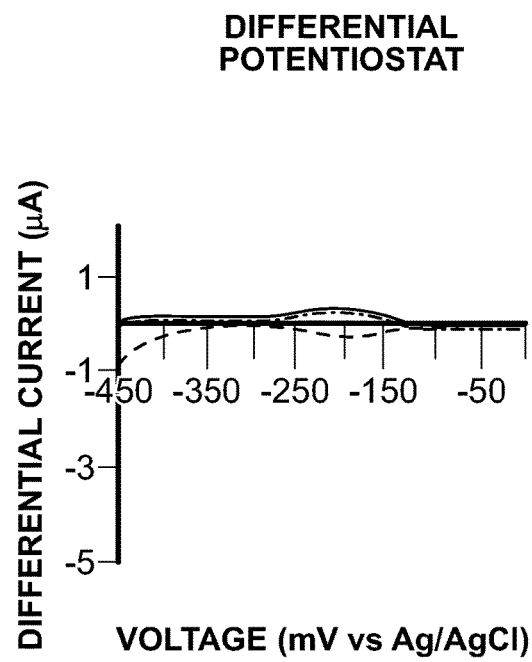
Figure 3C:
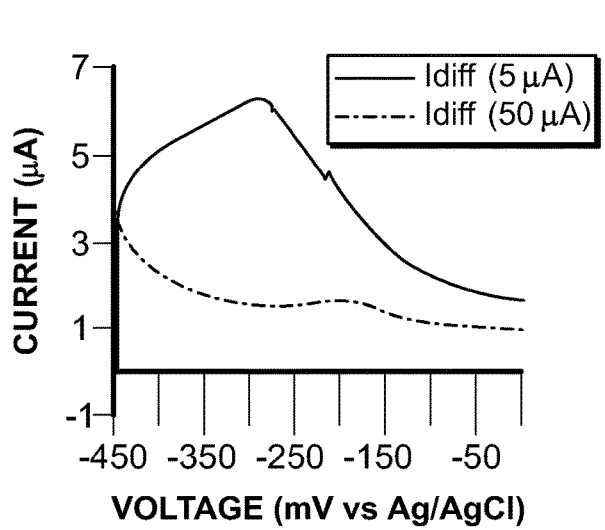
Figure 3D:
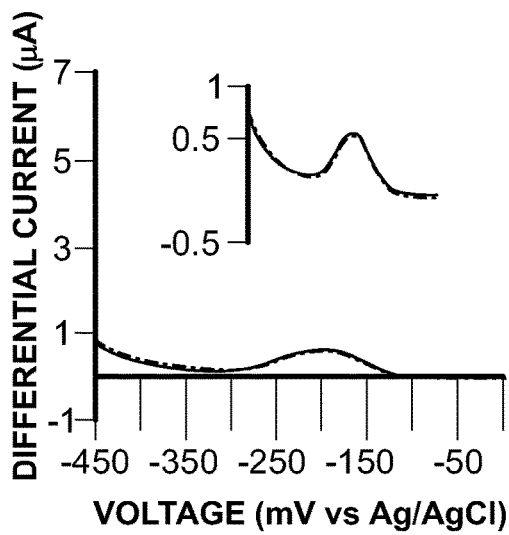

As can be seen in FIG. 3A, the conventional potentiostat 10 exhibits inconsistent currents and amplifier saturation at higher sensitivity settings (e.g., a 5 microamp range). As a result, the difference between forward current ($I_{fr}$) and reverse current ($I_{re}$) ($I_{diff}=I_{fr}-I_{re}$) shown in FIG. 3C is unusable at higher sensitivity settings. By contrast, as can be seen in FIG. 3B, the differential potentiostat 20 outputs a corrected response for both sensitivity settings (5 and 50 microamp ranges) that does not exhibit amplifier saturation. Because the background noise is removed prior to amplification, the differential potentiostat 20 is much less likely to reach saturation conditions than the conventional potentiostat 10. As can be seen in FIG. 3D, the difference current $I_{diff}$ has the same general shape at both lower and higher sensitivities for the differential potentiostat 20. As such, FIGS. 3A-3D illustrate that the differential potentiostat 20 reduces or eliminates background currents during the measurement, thereby allowing the use of wider detection ranges, higher sensitivities, and larger electrodes.

Figure 4A:
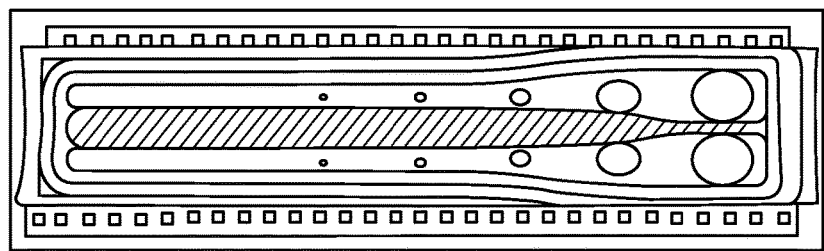
FIGS. 4A-E illustrate different sizes of diameter of working electrodes evaluated using square-wave voltammetry.
Figure 4B:
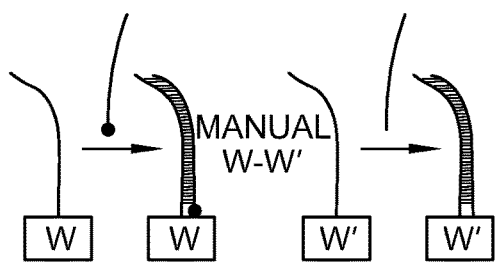
Figure 4C:
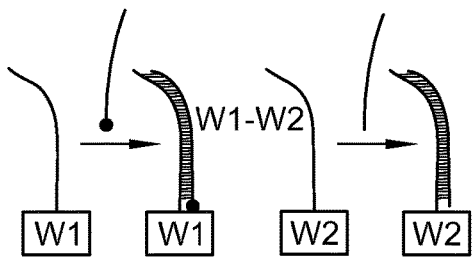
Figure 4D:
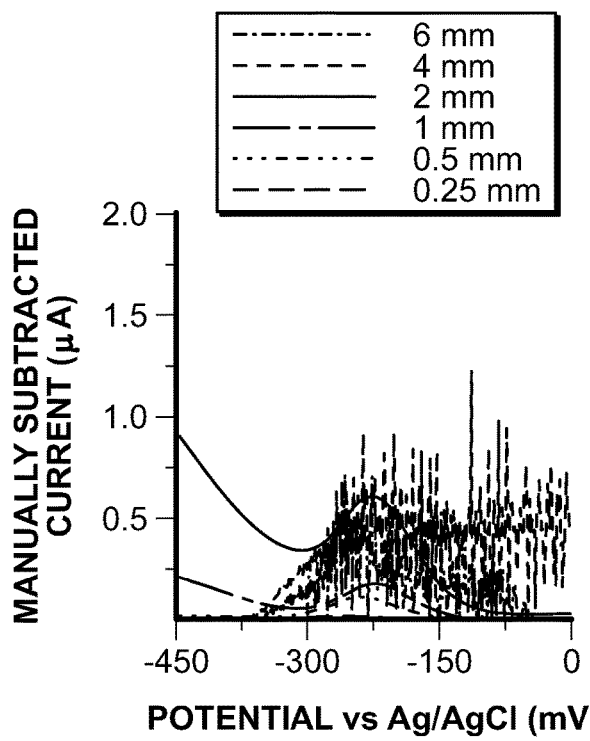
Figure 4E:
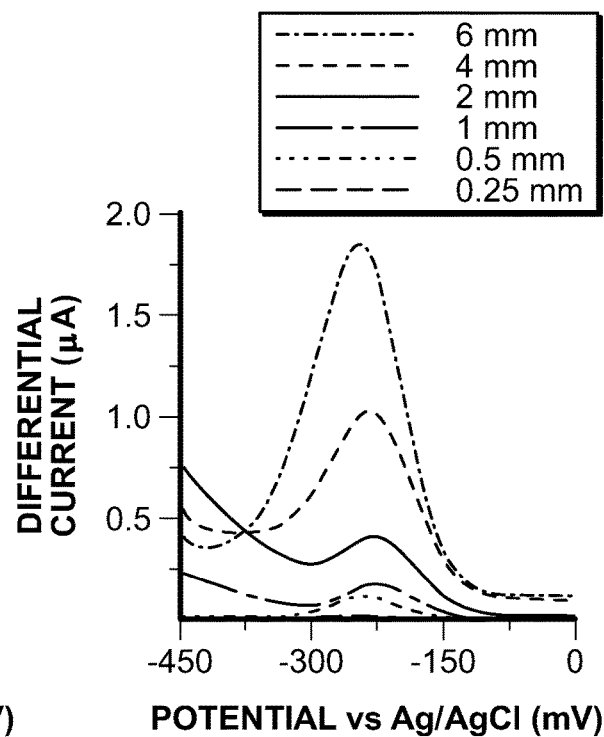

Referring now to FIGS. 4A-4E, different sizes of diameter of working electrodes were evaluated using the square-wave voltammetry. As shown in FIG. 4A, duplicate gold on glass working electrodes were fabricated, and a polydimethylsiloxane (PDMS) chamber was molded to contain the medium. Subsequently, 40 nucleotide thiolated DNA (thio-DNA) was immobilized on all working electrode surfaces. Complementary 40 nucleotide methylene blue-DNAs (MB-DNAs) were introduced to the first working electrode W1, while unlabeled complementary 40 nucleotide DNAs were introduced to the second working electrode W2 to provide an equivalent or similar capacitive background. Upon addition of the respective complementary DNAs to each working electrode, the current was measured by the square-wave voltammetry. With the conventional potentiostat 10, it was necessary to measure these currents separately, then manually subtract the results as shown in FIG. 4D. With the differential potentiostat 20, a continuous on-chip subtraction allowed a single measurement to be made at each working electrode diameter as shown in FIG. 4E. As can be seen in FIG. 4D, the conventional potentiostat 10 was only functional with electrode diameters in the range of 0.25 to 2 mm due to overwhelming capacitive current on larger electrodes. By contrast, as can be seen in FIG. 4E, the differential potentiostat 20 was functional throughout the entire range of 0.25 to 6 mm. In addition, FIGS. 4A-4E illustrates the accuracy in the differential potentiostat measurements because the non-saturated currents of the differential potentiostat 20 measured with the electrode diameters in the range of 0.25 to 2 mm were essentially equal to those of the conventional potentiostat 10. As such, FIGS. 4A-4E illustrates that wider detection ranges, higher sensitivities, and larger electrodes can be used with the differential potentiostat 20. Since the effect is highly dependent on an electrode surface area, the background reductions introduced by the differential potentiostat are extendable to electrodes of higher surface area (such as screen-printed electrodes, nanostructures electrodes, etc.), not necessarily only to electrodes with larger footprints.

Figure 5A:
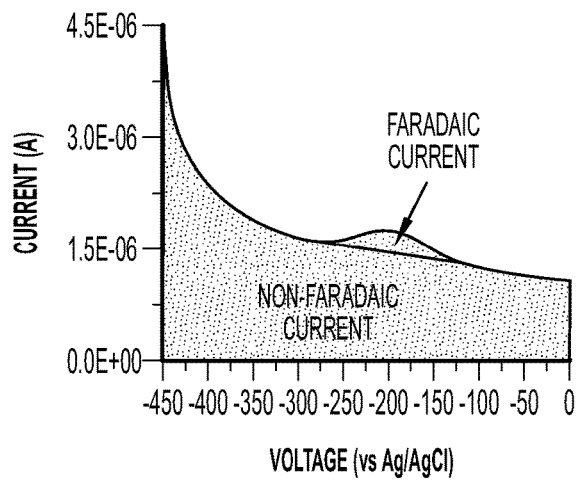
FIGS. 5A-D illustrate a reduction in square-wave voltammetry baseline current and noise by the differential potentiostat as compared to the conventional potentiostat.
Figure 5C:
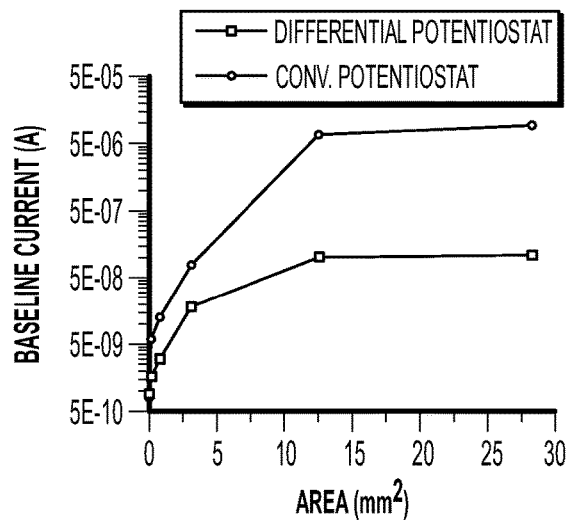
Figure 5B:
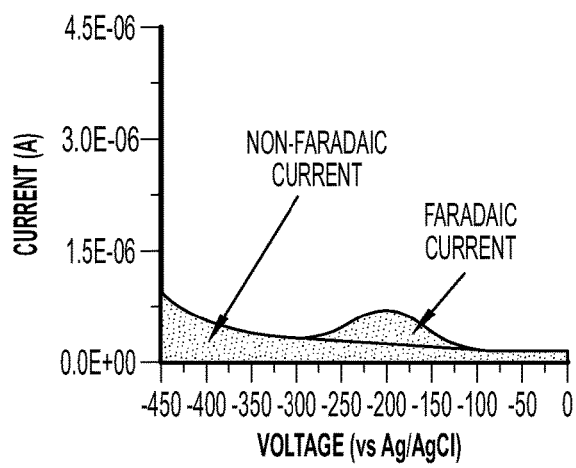
Figure 5D:
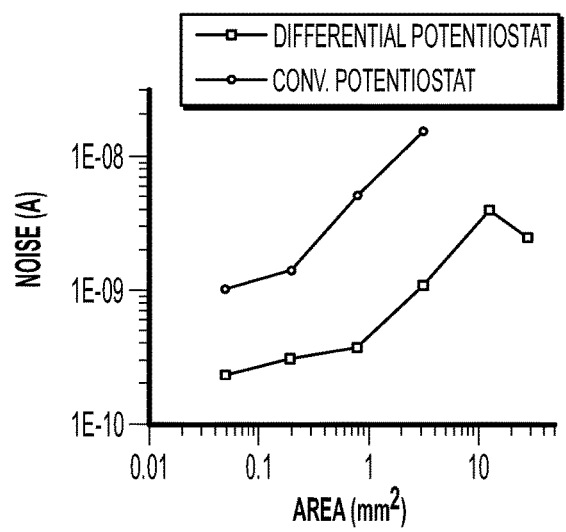

Referring now to FIGS. 5A-5D, the reduction in square-wave voltammetry baseline current by the differential potentiostat 20 is illustrated. The baseline current (i.e. capacitive current) and the faradaic current from the MB-DNA are indicated in FIGS. 5A and 5B. The conventional potentiostat 10 clearly shows much higher capacitive current, as shown in FIG. 5A, while the differential potentiostat 20 greatly reduces the capacitive current without altering faradaic current, as shown in FIG. 5B. The baseline current was then averaged between −70 mV and −80 mV for each and plotted versus electrode area, as illustrated in FIG. 5C. A reduction in baseline capacitive current of nearly two orders of magnitude was realized using the differential potentiostat 20 as compared to the conventional instrument 10. Due to the on-chip subtraction prior to complete amplification, the baseline noise was also shown to be reduced using the differential potentiostat 20. This noise was calculated by the standard deviation at the baseline between −60 mV to 0 mV of a MB-DNA square wave voltammogram. As shown in FIG. 5D, the conventional potentiostat noise increased with the surface area of the working electrode, and the two largest diameters are absent in the plot due to extreme noise forcing them out of range. The differential potentiostat output exhibited an average of 3.6-fold reduction in noise with its more favorable circuit configuration.

Figure 6:
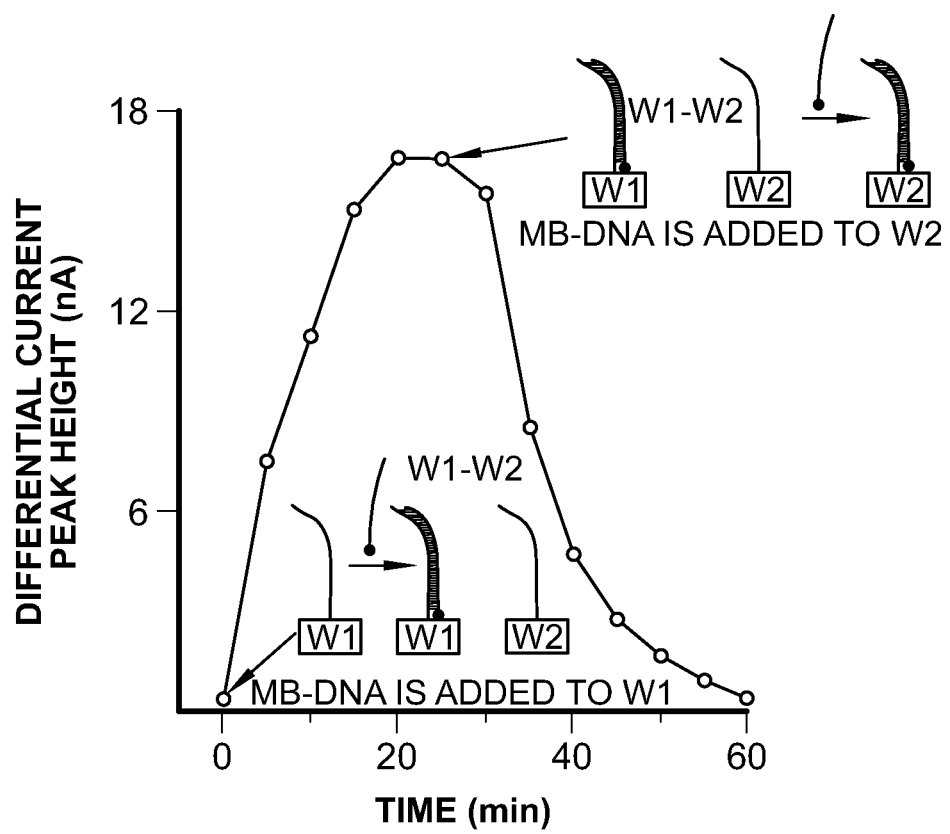
FIG. 6 is a graph representing differential currents measured by the differential potentiostat of FIG. 1B.

FIG. 6 provides another graph illustrating the operation of the differential potentiostat 20. As diagrammatically shown at the 0 minute mark of FIG. 6, a labeled target DNA strand was added only to a first working electrode W1 that was coated with a recognition element, while no target DNA strand was added to the second working electrode W2, which was also coated with the same recognition element. As can be seen in FIG. 6, the signal increased over time between 0 to 30 min. Subsequently, at about the 30 minute mark, the same labeled target DNA strand was added to the second working electrode W2. Since the output signal of the differential potentiostat 20 is proportional to the difference of the currents in the first working electrode W1 and the second working electrode W2, the differential current decreased back to zero over time, as shown in time period between 30 to 60 min. As such, FIG. 6 confirms that the output signal obtained from the differential potentiostat 20 is the difference in signals between the working electrodes W1, W2.

Figure 7:
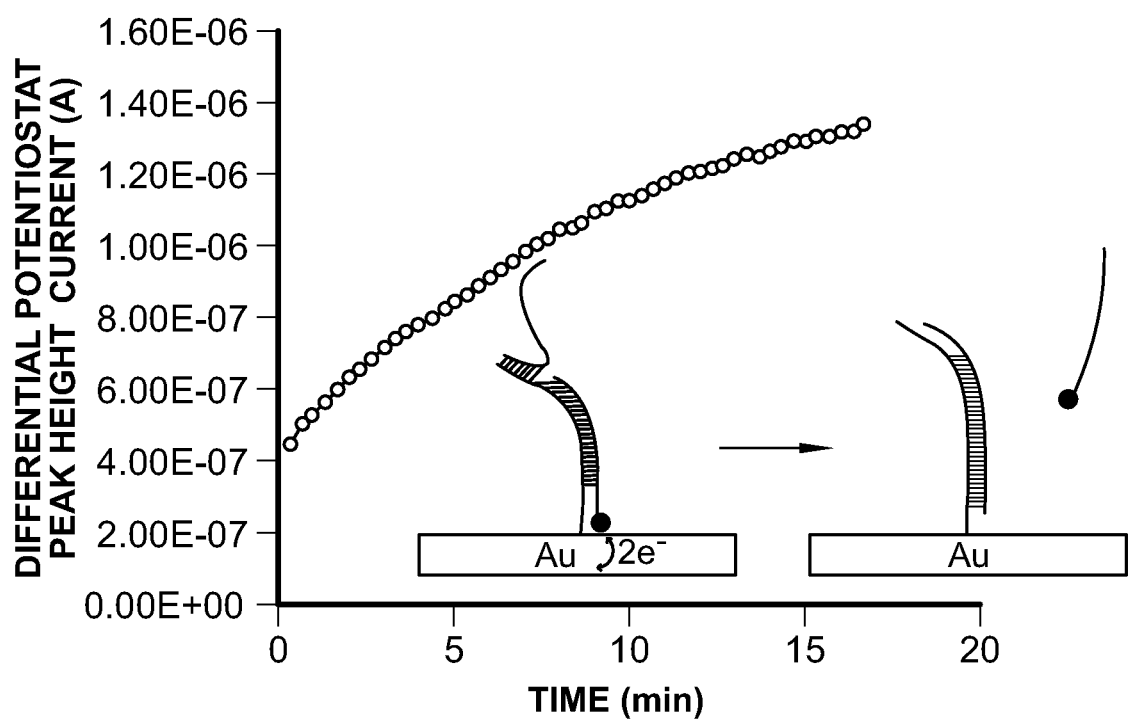
FIG. 7 is a graph representing differential currents measured by enabling signal-on readout from signal-off assay using the differential potentiostat of FIG. 1B.

It should be appreciated that, in some embodiments, the differential potentiostat 20 may allow significantly higher sensitivities to be achieved with various "signal-off" platforms. For example, as shown in FIG. 7, a "signal-off" sensor, in which a signal is reduced upon addition of target, can be converted to a "signal-on" sensor simply by controlling the choice of the first working electrode W1 versus the second working electrode W2 in the differential potentiostat 20.

Figure 8:
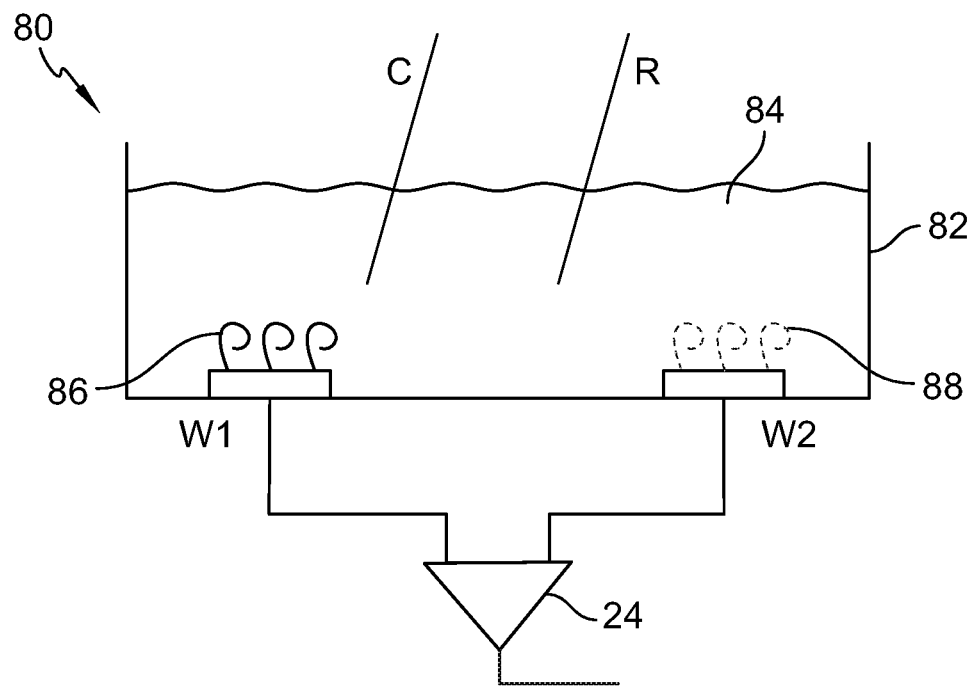
FIG. 8 is a diagrammatic representation of an exemplary embodiment of a first system that includes the differential potentiostat of FIG. 1B with both working electrodes positioned in one sample cell.
Figure 9:
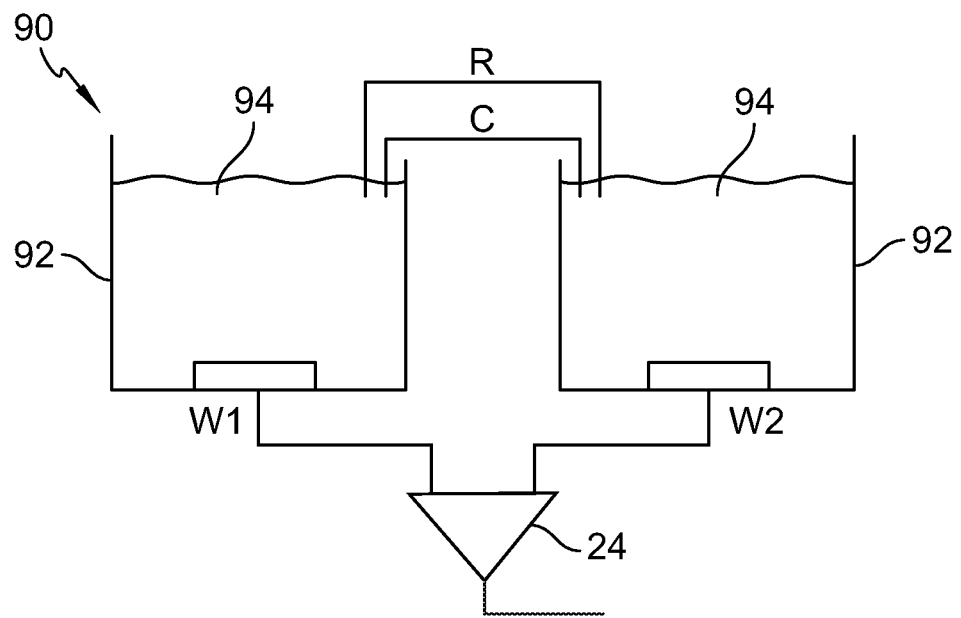
FIG. 9 is a diagrammatic representation of an exemplary embodiment of a second system that includes the differential potentiostat of FIG. 1B with each working electrode positioned in a separate sample cell.

Referring now to FIGS. 8 and 9, different embodiments of a system having the differential potentiostat 20 are shown. FIG. 8 represents a first embodiment of the system with the differential potentiostat 20. The system 80 includes a single sample cell 82 with at least two working electrodes W1 and W2. The first working electrode W1 is designed to measure a first signal responsive to a target molecule in the sample 84 and any background interferences and is coated with a first recognition element 86 (such as an aptamer, antibody, nucleic acid, etc.) that is to interact with the target molecule. The second working electrode W2 is configured to generate a second signal for background correction and is coated with a second recognition element 88. For example, the first working electrode W1 may be coated with a labeled recognition element 86, whereas the second working electrode W2 may be coated with an unlabeled recognition element 88. As discussed above, the output of the differential amplifier circuit 24 is proportional to the differences between the first and second signals.

FIG. 9 represents a second embodiment of the system with the differential potentiostat 20. The system 90 includes two sample cells 92. Each sample cell has one working electrode W1 or W2, and both sample cells are in contact with at least one counter electrode and one reference electrode. The first working electrode W1 is configured to measure a first signal responsive to a target molecule in the sample 94 and any background interferences. The second working electrode W2 is configured to generate a second signal for background correction. Again, as discussed above, the output of the differential amplifier circuit 24 is proportional to the differences between the first and second signals. It should be appreciated that, in some embodiments, the system 90 may include more than two sample cells and two working electrodes.

There are various methods for detecting a target molecule using the differential potentiostat 20. As discussed above, the target molecule is configured to interact with a recognition element. For example, different exemplary embodiments of the system 80 of FIG. 8 are illustrated in FIGS. 10A-10E. In such embodiments, the first working electrode W1 is coated with a first recognition element 86 (three of which are shown on the first working electrode W1 in FIGS. 10A-10E), and the second working electrode W2 (three of which are shown in dotted line on the second working electrode W2 in FIGS. 10A-10E) is coated with a second recognition element 88. The first recognition element 86 is configured to interact with the target molecule T, while the second recognition element 88 is configured to interact with the sample medium and provide equivalent or similar background signal compared to the first recognition element 86. However, it should be appreciated that only one or more pairs of the recognition element and target molecule that are electrochemically active will influence a signal that represents the target molecule T. To do so, an electrochemically active first recognition element, an electrochemically active second recognition element, an electrochemically active target molecule, or additional electrochemically active component C* that amplifies the presence of the target molecule is added to the sample 84.

FIG. 10A depicts a first embodiment of the system 80. In such embodiment, the system 80A includes an electrochemically active target molecule (T*, where * indicates that the target molecule is electrochemically active). For example, the target molecule may be represented by a small electrochemically active molecule such as dopamine. Alternatively, the target molecule may be labeled with an electrochemically labeled large molecule such as a protein. It should be appreciated that, in some embodiments, any electrochemically active or activated target with a variety of molecular sizes and shapes may be used. As shown in FIG. 10A, the electrochemically active target molecule T* will interact with the first recognition element 86 on the first working electrode W1 but does not interact with the second recognition element 88 on the second working electrode W2.

FIG. 10B illustrates a second embodiment of the system 80. In such embodiment, the system 80B includes a compound that interacts with the target molecule T that is labeled with an electrochemically active component C*. For example, the electrochemically active component C* may be a protein such as an electrochemically labeled antibody that specifically interacts with the target molecule T. The electrochemically active component C* may be any electrochemically active or activated component with a variety of molecular sizes and shapes that is configured to interact with the target molecule T. As shown in FIG. 10B, the electrochemically active component C* interacts with the target molecule T, which in turn interacts with the first recognition element 86 on the first working electrode W1 but does not interact with the second recognition element 88 on the second working electrode W2.

FIG. 10C illustrates a third embodiment of the system 80. In such embodiment, the system 80C includes the first and second recognition elements 86, 88 on the working electrodes W1 and W2, respectively, that are both electrochemically active or are both labeled with electrochemically active components. This allows the target molecule T to interact with the first recognition element 86 on the first working electrode W1 to affect the signal at the first working electrode W1 and be differentiated from signals at the second working electrode W2, at which the second recognition element is designed to not interact with the target.

FIG. 10D illustrates a fourth embodiment of the system 80. In such embodiment, the system 80D includes freely diffusing electrochemically active components are present in the sample cell for the purpose of increasing the difference between the first and second signals, thereby increasing the sensitivity of the system 80 toward target detection. For example, a small electrochemically active molecule C*, such as potassium ferricyanide, could be added to the sample medium at relatively high concentration. The interactions of the target molecule T with the first working electrode W1 surface can be differentiated from the lack of interactions at the second working electrode W2 surface through the current signals from freely diffusing potassium ferricyanide molecules C*. As a result, the final signal difference is amplified by the presence of potassium ferricyanide in the sample medium.

FIG. 10E illustrates a fifth embodiment of the system 80. In such embodiment, the system 80E includes a surface confined electrochemically active component C* on both working electrodes W1 and W2 in the sample cell to increase the difference between the first and second signals, thereby increasing the sensitivity of the system toward target detection. The system 80E is similar to the system 80D except that the electrochemically active component C* is tethered to the electrode surfaces, which permits dip-and-read type readout with the sensor. It should be appreciated that the system 80E may be advantageous in point-of-care applications.

Additionally, different exemplary embodiments of the system 90 of FIG. 9 are illustrated in FIGS. 11A-11J. In such embodiments, the first working electrode W1 may be coated with a recognition element 96 (three of which are shown on the first working electrode W1 in FIGS. 11A-11J), and the second working electrode W2 (three of which are shown on the second working electrode W2 in FIGS. 11A-11J) may also be coated with the recognition element 96. The recognition element 96 is configured to interact with the target molecule T. However, it should be appreciated that only one or more pairs of the recognition element and target molecule that are electrochemically active will influence a signal that represents the target molecule T. To do so, an electrochemically active first recognition element, an electrochemically active second recognition element, an electrochemically active target molecule, or additional electrochemically active component C* that amplifies the presence of the target molecule T is added to the sample 94.

FIG. 11A illustrates a first embodiment of the system 90. In such embodiment, the system 90A includes an electrochemically active target molecule T*. The target molecule T* is only introduced to one cell that contains the first working electrode W1. The second cell contains W2 for the purposes of generating background signals for downstream subtraction by the circuitry. As examples, the target molecule T* could be represented by a small electrochemically active molecule such as dopamine, an electrochemically labeled large molecule such as a protein, or any electrochemically active or activated target with a variety of molecular sizes and shapes. As shown in FIG. 11A, the electrochemically active target molecule T* will interact with the first working electrode W1 but does not interact with the second working electrode W2.

FIG. 11B illustrates a second embodiment of the system 90. In such embodiment, the system 90B includes the first and second working electrodes W1, W2 that are coated with an identical recognition element 96 and an electrochemically active target molecule T*. The target molecule is only introduced to one cell that contains the first working electrode W1. The recognition element 96 of the first working electrode W1 is configured to interact with the target molecules T* in the first sample cell. The recognition element 96 of the second working electrode W2 is configured to interact only with the medium in the second sample cell, providing the second signal for background correction. For example, both W1 and W2 (in both cells) could be coated with a target-recognizing aptamer (or antibody, etc.), where upon target binding at the first working electrode W1, the current from the labeled target can be differentiated from the background currents at the second working electrode W2.

FIG. 11C illustrates a third embodiment of the system 90. In such embodiment, the system 90C includes the first and second working electrodes that are coated with an identical recognition element 96, an electrochemically active target molecule T* in the first cell with the first working electrode W1, and an unlabeled target molecule T in the second cell with the second working electrode W2. The unlabeled target T at the second working electrode W2 permits improved background correction by subtracting any non-faradaic signals introduced by target binding at the first working electrode W1. For example, signal and background from an unlabeled protein target T binding to the second working electrode W2 can be subtracted from signal and background from a labeled protein target T* binding to the first working electrode W1, resulting in differential signal that is only from the labeled target. This embodiment may be particularly useful for removing capacitance changes introduced by target binding at the first working electrode W1, a correction that can be difficult to make with other methods.

FIG. 11D illustrates a fourth embodiment of the system 90. In such embodiment, the system 90D includes the first and second working electrodes W1, W2 that are coated with an identical recognition element 96, a labeled target molecule T* and an unlabeled target molecule T in the first cell with the first working electrode W1, and only the labeled target molecule in the second cell with the second working electrode W2. The recognition element 96 of the first working electrode W1 is configured to interact with both the labeled and unlabeled target molecules in the first sample cell, through a competitive binding mechanism. The recognition element of the second working electrode W2 is configured to interact with the labeled target molecule T* in the second sample cell, providing the second signal for background correction. For example, an antibody (or aptamer, etc.) specific for the target molecule could be coated onto the working electrodes W1, W2, and the labeled versions of the target molecule T* could be introduced to both cells. Upon introduction of the unlabeled target molecule T (representing the analyte), the electrochemical signal at the first working electrode W1 will be altered in proportion to the analyte amount, and that difference is measured with the differential potentiostat 20.

FIG. 11E illustrates a fifth embodiment of the system 90. In such embodiment, the system 90E is similar to the system 90A in FIG. 11A except that a target molecule T is neither electrochemically active nor labeled. Instead, an electrochemically active component C* that interacts with the target molecule T is added. For example, an antibody, aptamer, or binding molecule specific to the target T could be labeled with an electrochemically active component C*. Target introduction and signal output are similar to what was discussed above in regard to the system 90A.

FIG. 11F illustrates a sixth embodiment of the system 90. In such embodiment, the system 90F is similar to the system 90B in FIG. 11B except that the target molecule T is neither electrochemically active nor labeled. Instead, an electrochemically active component C* that interacts with the target molecule T is added. For example, an antibody, aptamer, or binding molecule specific to the target could be labeled with an electrochemically active component C*. Target introduction and signal output are similar to what was discussed above in regard to the system 90B.

Figure 11G:
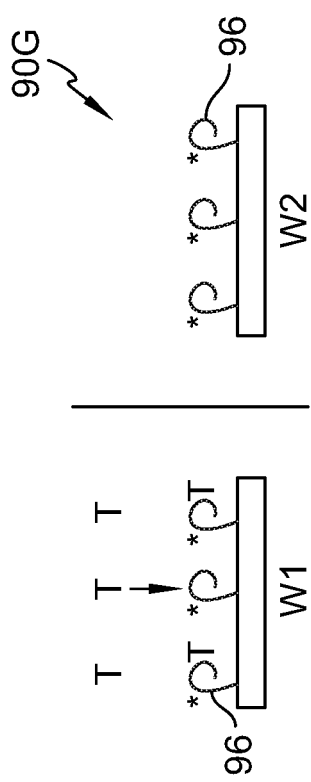

FIG. 11G illustrates a seventh embodiment of the system 90. In such embodiment, the system 90G includes the first and second working electrodes W1, W2 that are coated with an identical recognition element 96 and the target molecule T in the first cell with the first working electrode W1. The recognition elements on both working electrodes W1, W2 are electrochemically active. The recognition element of the first working electrode W1 is to interact with the target molecule T in the first sample cell. The recognition element of the second working electrode W2 is to interact only with the sample medium in the second sample cell, providing the second signal for background correction.

Figure 11H:
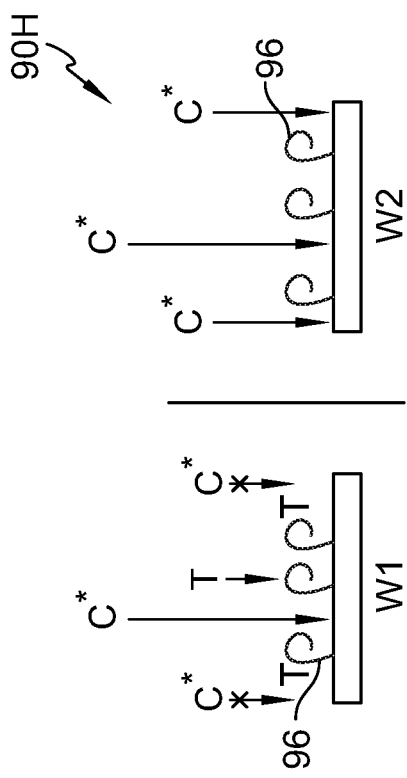

FIG. 11H illustrates an eighth embodiment of the system 90. In such embodiment, the system 90H includes the first and second working electrodes W1, W2 that are coated with an identical recognition element, a target molecule T in the first cell with the first working electrode W1, and freely diffusing electrochemically active components C* in both sample cells. The freely diffusing electrochemically active components C* are configured to increasing the difference between the first and second signals, thereby increasing the sensitivity of the system toward target detection. Similar to the system 90G, the recognition element of the first working electrode W1 is to interact with the target molecules T in the first sample cell. The recognition element of the second working electrode W2 is to interact only with the sample medium in the second sample cell, providing the second signal for background correction.

Figure 11I:
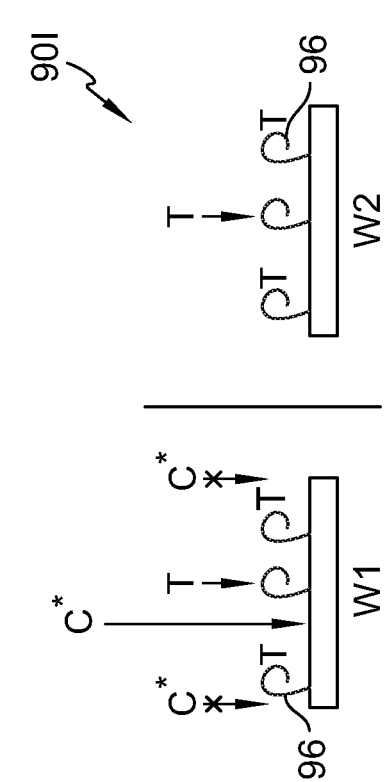

FIG. 11I illustrates a ninth embodiment of the system 90. In such embodiment, the system 90I includes the first and second working electrodes W1, W2 that are coated with an identical recognition element, target molecules T in both sample cells, and freely diffusing electrochemically active components C* only in the first sample cell. Again, the freely diffusing electrochemically active components C* are configured to increasing the difference between the first and second signals, thereby increasing the sensitivity of the system toward target detection. The recognition elements of the working electrodes W1, W2 are configured to interact with the target molecules T added to both sample cells. Further, freely diffusing electrochemically active components C* are present in only the first sample cell for the purpose of increasing the difference between the first and second signals, thereby increasing the sensitivity of the system toward target detection. It should be noted that, in the system 90I, the signal output prior to the addition of the target molecule T will not be corrected to zero, or "zeroed out," and will thus decrease upon target addition.

Figure 11J:
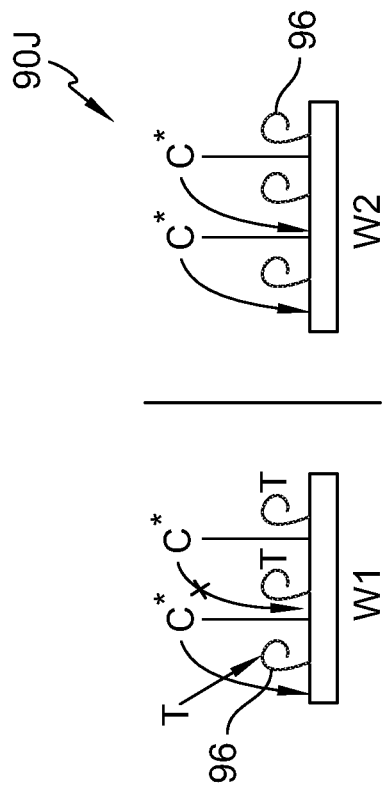

FIG. 11J illustrates a tenth embodiment of the system 90. In such embodiment, the system 90J includes the first and second working electrodes W1, W2 that are coated with an identical recognition element and a target molecule T in the first cell with the first working electrode W1. Additionally, the system 90J includes surface confined electrochemically active components C* on both working electrodes in both sample cells for the purpose of increasing the difference between the first and second signals, thereby increasing the sensitivity of the system toward target detection. Again, such configuration permits dip-and-read type readouts with the sensor, which may be advantageous in point-of-care applications.

As used in the present disclosure, a sample may be any substance that contains a target molecule of interest present in a sample medium. The target molecule can be electrochemically inactive or electrochemically active. For examples, the target molecule may include small molecules (e.g. glucose, dopamine, amino acids, antibiotics, toxins, etc.), nucleic acids (e.g. DNA, RNA, aptamers, etc.), peptides, proteins (e.g. biomarkers, antibodies, protein complexes, etc.), particles (e.g. nanoparticles, cells, viruses, etc.), or volatile substances (e.g. gases, low melting temperature substances, etc.). The sample medium may be a solvent (e.g. water, buffer, organic solvent, gas, etc.) or a complex matrix (e.g. blood, serum, biological tissue, cell lysate, food, soil, river water, etc.). A recognition element may be a molecule, complex, or particle that is configured to bind to, or otherwise interacts with, the target of interest. For example, the recognition element may be chelating agents, nucleic acids, peptides, proteins, antibodies, aptamers, particles, cells, or synthetic agents. Moreover, it should be appreciated that, in some embodiments, multiple electrochemically active components may be used for sequential or simultaneous detection of multiple target molecules.

Although certain illustrative embodiments and graphical illustrations have been described in detail above, variations and modifications exist within the scope and spirit of this disclosure as described and as defined in the following claims.

The invention claimed is:

1. Apparatus for target molecule detection comprising:
a sample cell configured to receive a sample;
a reference electrode in communication with the sample cell;
a counter electrode in communication with the sample cell;
a first working electrode in communication with the sample cell, wherein the first working electrode is coated with a first recognition element that is labeled with an electrochemically active component and is configured to interact with a target molecule in the sample, and wherein the first working electrode is configured to measure a first signal responsive to interaction of the first recognition element with the target molecule;
a first current-to-voltage converter circuit coupled to the first working electrode and configured to convert the first signal to a first voltage signal, the first signal being current measured at the first working electrode;
a second working electrode in communication with the sample cell, wherein the second working electrode is coated with a second recognition element that is not labeled with the electrochemically active component and is configured to interact with the target molecule in the sample, and wherein the second working electrode is configured to measure a second signal indicative of background noise including non-faradaic current from the sample;
a second current-to-voltage converter circuit coupled to the second working electrode and configured to convert the second signal to a second voltage signal, the second signal being current measured at the second working electrode; and
a differential amplifier circuit configured to generate a modified signal that is proportional to a voltage difference between the first and second voltage signals, wherein the modified signal indicates an amount of the target molecule present in the sample.

2. The apparatus of claim 1, wherein the first and second working electrodes are prepared using the same technique(s) other than the coating the second working electrode with the second recognition element instead of the first recognition element.

3. The apparatus of claim 1, wherein the background noise includes at least one of capacitive current, electrical noise, environmental noise, chemical interferences, biological interferences, and temperature effects.

4. The apparatus of claim 1, wherein the modified signal is proportional to an instantaneous difference between the first and second signals.

5. The apparatus of claim 1, wherein the first recognition element is the same as the second recognition element.

6. Apparatus for target molecule detection comprising:
a first sample cell configured to receive a target molecule in a medium;
a second sample cell configured to receive the medium with no target molecule;
a reference electrode in communication with the first and second sample cells;
a counter electrode in communication with the first and second sample cells;
a first working electrode in communication with the first sample cell wherein the first working electrode is coated with a first recognition element that is configured to interact with the target molecule, the first working electrode being configured to measure a first signal responsive to interaction of the first recognition element with the target molecule wherein the first sample cell further includes an electrochemically active molecule coupled to the first recognition element, and wherein the second sample cell does not include the electrochemically active molecule;
a second working electrode in communication with the second sample cell, wherein the second working electrode is coated with a second recognition element that is configured to interact with the target molecule, the second working electrode being configured to measure a second signal indicative of background noise including non-faradic current, from the medium; and
a differential amplifier circuit configured to generate a modified signal that is proportional to a difference between the first and second signals, wherein the modified signal indicates an amount of the target molecule present in the first sample cell.

7. The apparatus of claim 6, wherein the first and second working electrodes are prepared using the same technique(s).

8. The apparatus of claim 6, wherein the second signal indicates background noise from the medium, the background noise includes at least one of capacitive current, electrical noise, environmental noise, chemical interferences, biological interferences, and temperature effects.

9. The apparatus of claim 6, wherein the modified signal is proportional to an instantaneous difference between the first and second signals.

10. The apparatus of claim 6 further comprising:
a first current-to-voltage converter circuit coupled to the first working electrode and configured to convert the first signal to a first voltage signal, the first signal being current measured at the first working electrode; and
a second current-to-voltage converter circuit coupled to the second working electrode and configured to convert the second signal to a second voltage signal, the second signal being current measured at the second working electrode;
wherein the modified signal generated by the differential amplifier circuit is proportional to a voltage difference between the first and second voltage signals.

11. The apparatus of claim 6, wherein the first recognition element is the same as the second recognition element.

12. Apparatus for target molecule detection comprising:
a first sample cell configured to receive a target molecule in a medium;
a second sample cell configured to receive the medium with no target molecule;
a reference electrode in communication with the first and second sample cells;
a counter electrode in communication with the first and second sample cells;
a first working electrode in communication with the first sample cell wherein the first working electrode is coated with a first recognition element that is configured to interact with the target molecule, the first working electrode being configured to measure a first signal responsive to interaction of the first recognition element with the target molecule, wherein the target molecule is labeled with an electrochemically active component;
a second working electrode in communication with the second sample cell, wherein the second working electrode is coated with a second recognition element that is configured to interact with the target molecule, the second working electrode being configured to measure a second signal indicative of background noise including non-faradic current, from the medium; and
a differential amplifier circuit configured to generate a modified signal that is proportional to a difference between the first and second signals, wherein the modified signal indicates an amount of the target molecule present in the first sample cell.

13. Apparatus for target molecule detection comprising:
a first sample cell configured to receive a target molecule in a medium;
a second sample cell configured to receive the medium with no target molecule;
a reference electrode in communication with the first and second sample cells;
a counter electrode in communication with the first and second sample cells;
a first working electrode in communication with the first sample cell wherein the first working electrode is coated with a first recognition element that is configured to interact with the target molecule, further wherein the first working electrode is labeled with an electrochemically active component, the first working electrode being configured to measure a first signal responsive to interaction of the first recognition element with the target molecule;
a second working electrode in communication with the second sample cell, wherein the second working electrode is coated with a second recognition element that is configured to interact with the target molecule, further wherein the second working electrode is unlabeled with any electrochemically active component, the second working electrode being configured to measure a second signal indicative of background noise including non-faradic current, from the medium; and
a differential amplifier circuit configured to generate a modified signal that is proportional to a difference between the first and second signals, wherein the modified signal indicates an amount of the target molecule present in the first sample cell.

14. A method of target molecule detection comprising:
simultaneously obtaining a first signal from a first working electrode coated with a first recognition element configured to interact with a target molecule, and coupled to an electrochemically active component to generate a target-dependent faradaic current when the target molecule interacts with the first recognition element, and a second signal from a second working electrode coated with a second recognition element configured to interact with the target molecule, wherein the second recognition element is not coupled to an electrochemically active component, to generate a non-faradaic current when the target molecule interacts with the second recognition element, wherein the first signal is responsive to interaction of the first recognition element with the target molecule in a sample, and the second signal is indicative of background noise from the sample;
converting the first signal to a first voltage signal, the first signal being current measured at the first working electrode;
converting the second signal to a second voltage signal, the second signal being current measured at the second working electrode; and
generating a modified signal that is proportional to an instantaneous voltage difference between the first and second voltage signals, wherein the modified signal indicates an amount of the target molecule present in the sample.

15. The method of claim 14, wherein: the first and second working electrodes are both in communication with a sample cell receiving the sample.

16. The method of claim 14, wherein:
the first working electrode is in communication with a first sample cell receiving a target molecule in a medium, wherein the first working electrode is coated with a first recognition element that is labeled with an electrochemically active component and interacts with the target molecule; and
the second working electrode is in communication with a second sample cell receiving the target molecule in the medium, wherein the second working electrode is coated with a second recognition element that is to interact with the target molecule and is unlabeled with an electrochemically active component.

17. The method of claim 14, wherein the first recognition element is the same as the second recognition element.

* * * * *